(12) United States Patent
Mueller et al.

(10) Patent No.: US 11,691,960 B2
(45) Date of Patent: Jul. 4, 2023

(54) 2-[THIOPHEN-2-YL)FORMAMIDO]-N-(PHENYL)-2-METHYLPROPANAMIDE DERIVATIVES AND THE USE THEREOF AS MEDICAMENT

(71) Applicant: Boehringer Ingelheim International GmbH, Ingelheim am Rhein (DE)

(72) Inventors: Stephan Georg Mueller, Warthausen (DE); Kelly Allers, Biberach an der Riss (DE); Klaus Klinder, Oggelshausen (DE); Ursula Mueller-Vieira, Biberach an der Riss (DE); Henning Priepke, Warthausen (DE); Alexander Pautsch, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 17/518,608

(22) Filed: Nov. 4, 2021

(65) Prior Publication Data
US 2022/0144796 A1 May 12, 2022

(30) Foreign Application Priority Data
Nov. 6, 2020 (EP) .................................... 20206286

(51) Int. Cl.
| | | |
|---|---|---|
| C07D 333/38 | (2006.01) | |
| A61K 31/44 | (2006.01) | |
| A61K 45/06 | (2006.01) | |
| A61K 31/381 | (2006.01) | |

(52) U.S. Cl.
CPC .......... *C07D 333/38* (2013.01); *A61K 31/381* (2013.01); *A61K 31/44* (2013.01); *A61K 45/06* (2013.01)

(58) Field of Classification Search
None
See application file for complete search history.

(56) References Cited

U.S. PATENT DOCUMENTS

| | | |
|---|---|---|
| 7,058,024 B1 | 6/2006 | Koay |
| 7,476,663 B2 | 1/2009 | Pfau et al. |
| 7,563,786 B2 | 7/2009 | Priepke et al. |
| 7,732,466 B2 | 6/2010 | Pfau et al. |
| 2005/0256107 A1 | 11/2005 | Pfau et al. |
| 2005/0277628 A1 | 12/2005 | Pfau et al. |
| 2013/0184256 A1 | 7/2013 | Priepke et al. |
| 2015/0196533 A1 | 7/2015 | Mao et al. |

FOREIGN PATENT DOCUMENTS

| | | |
|---|---|---|
| CN | 101843618 | 9/2010 |
| WO | 2005111013 A1 | 11/2005 |
| WO | 2005111014 A1 | 11/2005 |
| WO | 2005111029 A1 | 11/2005 |
| WO | 2006034822 A1 | 4/2006 |
| WO | 2007003536 A1 | 1/2007 |

OTHER PUBLICATIONS

International Search Report for corresponding application, PCT/EP2021/080572, dated Feb. 1, 2022.
Isbarn, Androgen Deprivation therapy, EAU, vol. 55, 2009.
Shi, Population Pharmacokinetic and Pharmcodynamic Modeling, ACCP, 2016.
Beatty, First in Human Phase I study of the Oral Inhibitor of Indoleamine 2,3-Dioxygenase-1 Epacadostat, Clinical Cancer Research, 2017.
Clinical Drug Interaction Studies, FDA, 2020.
Kalvass, Pharmacokinetics and Pharmacodynamics of Seven Opiods in P-Glycoprotein-Competent Mice, The J. of Pharmcology, 2007.
Udenaes, On the rate and ectent of drug delivery to the Brain, Pharma Research, vol. 25, 2008.
Liu, Progress in Brain Penetration Evaluation in Drug Discovery and Development, The J. Of Pharmacology, 2008.
Di, Strategies to assess blood-brain barrier penetration, Expert Opinion on Drug Discovery, 2008.
Doran, The impact of P-glycoprotein on the disposition of drugs targeted for indications of the central nervous system, The American Society for Pharmacology and Exp. Therapeutics, 2005.
Sadeque, Increased drug delivery to the brain by P-glycoprotein inhibition, Pharcokinetics, 2000.
Bauer, Approaching complete inhibition of P-glycoprotein ar the human blood brian barrier, J. of Cerebral blood and Metabolism, 2015.
Kodaira, Quantitative evaluation of the Impact of Active Efflux by P-GLycoprotein and Breast Cancer Resistance Protein at the Blood-Brian Barrier on the Predictability of the Unbound Concentrations of Drugs, Journal of Pharmacology and experimental Therapeutics, 2011.

(Continued)

*Primary Examiner* — Bong-Sook Baek
(74) *Attorney, Agent, or Firm* — Shelley A. Jones

(57) ABSTRACT

The present invention relates to novel 2-[thiophen-2-yl)formamido]-N-(phenyl)-2-methylpropanamides of formula A

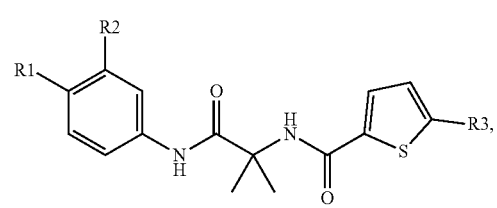

and pharmaceutically acceptable salts thereof, wherein $R^1$ to $R^3$ are as defined herein. The invention also relates to processes for the preparation of these compound, pharmaceutical compositions containing them and their use in therapy, particularly in the treatment or prevention of conditions in which inhibition of the indoleamine 2,3-dioxygenase 1 (IDO1) enzyme may be beneficial.

18 Claims, No Drawings

(56) References Cited

OTHER PUBLICATIONS

Greenberg, Etoposide, Vincristine, and Cyclosporin a with Standard dose radiation therapy in newly diagnosed diffuse intrinsic brainstem gliomas, Pediatric Blood cancer, 2005.

Sugimoto, Retrospective Analysis of P-Glycoprotein-Mediated Drug-Drug interactions at the Blood-Brian Barrier in Humans, Drug Metabolism and Disposition, 2013.

Sieger, pH-dependent solubility and Permeability profiles, Euro. J. of Pharma Sciences, 2017.

Liu, Correlation between membraine Protein Expression levels and Transcellular Transport activity for Breast cancer Resistance Protein, Drug metabolism and Disposition, 2017.

Doan, Passive Permeability and P-glycoprotein-mediated Efflux Differentiate central nervous system and non-CNS marketed drugs, J. of Pharmacology and Experimental Therapeutics, 2002.

Jeffery, Challenges for Bloos-Brain barrier Xenobiotica screening, 2007.

Qin, IDO and TDO as potential therapeutic target in different types of depression, Metabolic Brain disease, 2018.

Ye, Role of IDO and TDO in cancersand related diseases, J. of cancer, 2019.

Badaway, KyureninePathway of Tryptophan Metabolism, Int. J. of Tryptohan Research, vol. 10, 2017.

Wang, Tryptophan-kynurenine pathway is disregulated in inflammation, Frontiers in Bioscience, 2015.

Sasongo, Imaging P-glycoprotein transport activity at the human blood-brain barrier with positron emission tomograpgy, Pharmacokinetics and Drug Disposition, 2005.

Filho, IDO chronic immune activation and tryptophan metbolic pathway, Progress in Neuropsychopharmacology, 2018.

Cui, Muscle to Brain Partitioning as Measure of Transporter-Mediated Efflux at the Rat Blod-Brain Barrier-MDPI, vol. 11, 2019.

2-[THIOPHEN-2-YL)FORMAMIDO]-N-(PHENYL)-2-METHYLPROPANAMIDE DERIVATIVES AND THE USE THEREOF AS MEDICAMENT

FIELD OF THE INVENTION

The present invention relates to novel 2-[thiophen-2-yl) formamido]-N-(phenyl)-2-methylpropanamides of formula A

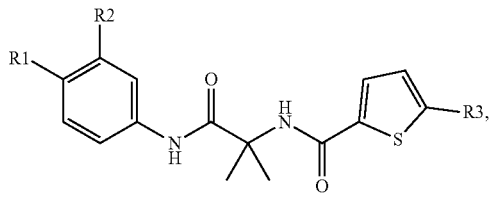

processes for their preparation, pharmaceutical compositions containing them and their use in therapy, particularly in the treatment or prevention of conditions in which inhibition of the indoleamine 2,3-dioxygenase 1 (IDO1) enzyme may be beneficial.

The compounds of the invention according to formula A are IDO1 inhibitors.

BACKGROUND OF THE INVENTION

Extensive studies over the past twenty years have indicated that IDO1 enzymatic activity may play a role in producing symptoms of numerous neurological and psychiatric disorders including Major Depressive Disorder, Schizophrenia, Huntington's Disease, Parkinson's Disease, Amyotrophic lateral sclerosis, multiple sclerosis, chronic pain, and obesity.

Inhibition of IDO1 has largely been applied to oncology indications up to now. The compounds utilized for these studies are largely non-brain penetrant compounds, excluding them from use for neurological or psychiatric treatments. In these conditions, IDO1 has increased expression in the immune cells of the brain, mainly microglia and infiltrating macrophages. The resulting changes in tryptophane metabolites in the kynurenine pathway (e.g. quinolinic acid, kynurenic acid) affect brain function. For this reason, the IDO1 enzyme to target to treat these diseases is located in the brain.

The compounds disclosed herein have been developed for use in central nervous system diseases and therefore show good permeability, low/no efflux, low clearance and pharmacokinetic properties suitable for once-daily treatment. The central nervous system diseases may include neuropsychiatric and neurobehavioral disorders, neurodegenerative diseases, detrimental consequences of increased IDO1 activity following head trauma or cerebrovascular events. The compounds are suitable for use as adjunctive therapies in such neurological indications, showing a metabolic profile that is minimized for drug-drug interaction potential.

IDO1 activity is also known to play a role in producing symptoms of numerous somatic disorders due to its upregulation during inflammatory states. IDO1 inhibition may have beneficial effects following bacterial and viral infection such as tuberculosis and human immunodeficiency virus (HIV), and meningitis. These compounds, being optimized for central nervous system action, are suited for treating both the central and peripheral symptoms in these disorders, for example cognitive and affective impact of HIV, or long term neurological consequences of meningitis. Inflammation of the retina is observed in retinal diseases such as diabetic retinopathy and geographic atrophy, with a consequent increase in IDO1 thought to lead to tissue degeneration. Metabolic disorders such as obesity have been linked to increased inflammation and IDO1, suggesting inhibition may be beneficial.

SUMMARY OF THE INVENTION

WO2006/034822 discloses compounds of formula (I) that are inhibitors of human Factor Xa being useful as antithrombotic agents.

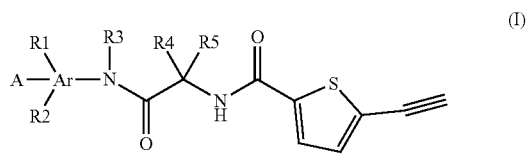

The compounds of the present invention differ structurally from formula (I) of WO2006/034822 in that they contain:
  i) a 5-chloro-thiophene or a 5-bromo-thiophene moiety in place of a 5-ethynyl-thiophene moiety; and
  ii) a phenyl ring which is substituted with one or two halogens in place of a phenyl ring which is substituted with a heterocyclic moiety A.

Formula (I) encompasses the specific example 5-ethynyl-N-{1-trifluoromethyl-1-[3-methyl-4-(3-oxomorpholin-4-yl) phenylcarbamoyl]ethyl}thiophene-2-carboxamide (WO2006/034822 page 91, lines 7-8, 5-Ethinyl-thiophen-2-carbonsäure-N-{1-trifluormethyl-1-[3-methyl-4-(3-oxo-morpholin-4-yl)-phenylcarbamoyl]-ethyl}-amid) which additionally exhibits a trifluoromethyl moiety within formula (I).

Example 5-ethynyl-N-{1-trifluoromethyl-1-[3-methyl-4-(3-oxomorpholin-4-yl)phenylcarbamoyl]ethyl}thiophene-2-carboxamide (WO2006/034822 page 91, lines 7-8, 5-Ethinyl-thiophen-2-carbonsaure-N-{1-trifluormethyl-1-[3-methyl-4-(3-oxo-morpholin-4-yl)-phenylcarbamoyl]-ethyl}-amid)

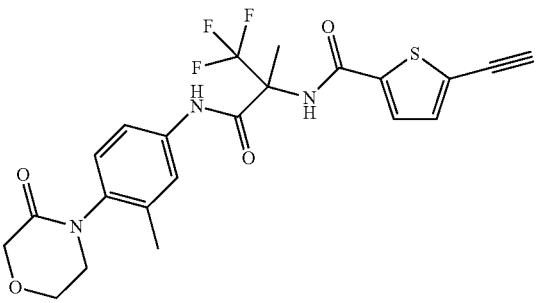 [SMILES: C#Cc1ccc(C(=O)NC(C)(C(=O)Nc2ccc(N3CCOCC3=O)c(C)c2)C(F)(F)F)s1]

Example 5-ethynyl-N-{1-trifluoromethyl-1-[3-methyl-4-(3-oxomorpholin-4-yl)phenylcarbamoyl]ethyl}thiophene-2-carboxamide of WO2006/034822 (page 91, lines 7-8, 5-Ethinyl-thiophen-2-carbonsaure-N-{1-trifluormethyl-1-[3-methyl-4-(3-oxo-morpholin-4-yl)-phenylcarbamoyl]-ethyl}-amid) inhibits the human Factor Xa enzyme and shows a high efflux ratio.

Inhibition of the human Factor Xa enzyme is associated with undesired serious side effects such as extended bleeding. Currently available Factor Xa inhibitor medications (such as Rivaroxaban and Apixaban) are used as antithrombotic agents to prevent deep vein thrombosis, pulmonary emboli, and blood clots in atrial fibrillation. For a fast reversal of the effect an antidote has been developed (andexanet alfa). Additional use of Factor Xa inhibitors may include CNS indications such as neurodegeneration.

The compounds of the present invention differ structurally from formula (I) of WO2006/034822 in that they contain:
  i) a 5-chloro-thiophene or a 5-bromo-thiophene moiety in place of a 5-ethynyl-thiophene moiety; and
  ii) a phenyl ring which is substituted with one or two halogens in place of a phenyl ring which is substituted with a heterocyclic moiety A.

The structural difference unexpectedly results in an increase in selectivity of IDO1 inhibition over the human Factor Xa enzyme and in a low efflux ratio in the MDCK-MDR1 cell assay whereas 5-ethynyl-N-{1-trifluoromethyl-1-[3-methyl-4-(3-oxomorpholin-4-yl)phenylcarbamoyl]ethyl}thiophene-2-carboxamide of WO2006/034822 (page 91, lines 7-8, 5-Ethinyl-thiophen-2-carbonsaure-N-{1-trifluormethyl-1-[3-methyl-4-(3-oxo-morpholin-4-yl)-phenylcarbamoyl]-ethyl}-amid) inhibits the human Factor Xa enzyme and shows a high efflux ratio (Table 3a).

The objective technical problem is thus to provide potent, selective, metabolically stable, and brain penetrating IDO1 inhibitors.

According to the present invention, the compounds disclosed herein have surprisingly been found to be potent, selective, metabolically stable, and brain penetrating IDO1.

Due to their potent inhibition of IDO1, increased selectivity over the human Factor Xa enzyme and low in vitro efflux, compounds of the present invention are expected to show favorable brain penetration, which is required for efficacious drugs targeting the brain, and to have an acceptable window between efficacy and undesired serious side effects such as extended bleeding.

Consequently, compounds of the present invention must be more viable for human use.

WO2007/003536 discloses compounds of formula (I) that are inhibitors of human Factor Xa being useful as antithrombotic agents.

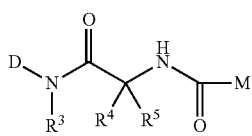
(I)

Formula (I) encompasses the specific examples 4, 6, and 159 which exhibit a heterobicyclic moiety D within formula (I), in contrast to a highly distinct monocyclic aromatic moiety within formula A.

Example 4 (Page 66)

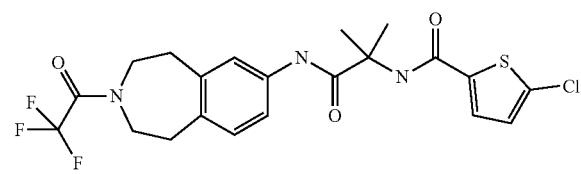 [SMILES: CC(C)(NC(=O)c1ccc(Cl)s1)C(=O)Nc1ccc2c(c1)CCN(C(=O)C(F)(F)F)CC2]

Example 6 (Page 68)

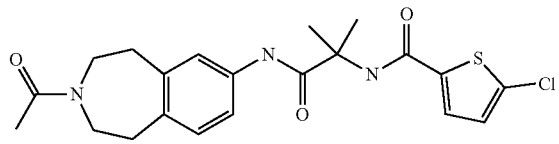 [SMILES: CC(=O)N1CCc2ccc(NC(=O)C(C)(C)NC(=O)c3ccc(Cl)s3)cc2CC1]

Example 159 (Page 137)

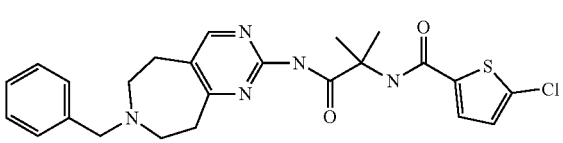 [SMILES: CC(C)(NC(=O)c1ccc(Cl)s1)C(=O)Nc1ncc2c(n1)CCN(Cc1ccccc1)CC2]

Inhibition of the human Factor Xa enzyme is associated with undesired serious side effects such as extended bleeding. Currently available Factor Xa inhibitor medications (such as Rivaroxaban and Apixaban) are used as antithrombotic agents to prevent deep vein thrombosis, pulmonary emboli, and blood clots in atrial fibrillation. For a fast reversal of the effect an antidote has been developed (andexanet alfa). Additional use of Factor Xa inhibitors may include CNS indications such as neurodegeneration.

The compounds of the present invention differ structurally from formula (I) of WO2007/003536 in that they contain a phenyl ring which is substituted with one or two halogens in place of a heterobicyclic moiety D.

The structural difference unexpectedly results in an increase in metabolic stability in human hepatocytes and in no in vitro efflux in the MDCK-MDR1 cell assay—and for Examples 3 and 4 in no in vivo efflux—whereas examples 4, 6 and 159 of WO2007/003536 show a low metabolic stability in human hepatocytes and/or high in vitro efflux ratio (Table 3b), and additionally a high in vivo efflux (Table 7).

The objective technical problem is thus to provide potent, selective, metabolically stable, and brain penetrating IDO1 inhibitors.

According to the present invention, the compounds disclosed herein have surprisingly been found to be potent, selective, metabolically stable, and brain penetrating IDO1 inhibitors.

Due to their potent inhibition of IDO1, increased selectivity over the human Factor Xa enzyme and low in vitro efflux, compounds of the present invention are expected to show favorable brain penetration, which is required for efficacious drugs targeting the brain, and to have an acceptable window between efficacy and undesired serious side effects such as extended bleeding.

Consequently, compounds of the present invention must be more viable for human use.

WO98/22432 discloses compounds of the formula (I) having antiandrogenic activity being useful as a prophylactic or therapeutic agent for prostatic cancer, prostatic hypertrophy, defemination, hypertrichosis, bald head, acne, and seborrhea.

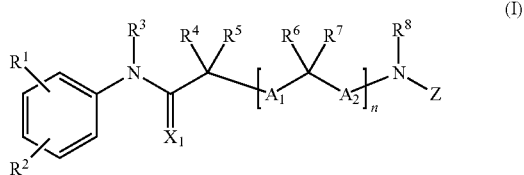

Formula (I) encompasses the specific examples 53 and 86 which exhibit a thiophene substructure within group Z (Table 1).

TABLE 1

Examples 53 and 86 of WO98/22432 exhibiting a thiophene substructure within group Z of formula (I).

| Example no. in WO98/22432 | Structure |
|---|---|
| 53 (page 38) | 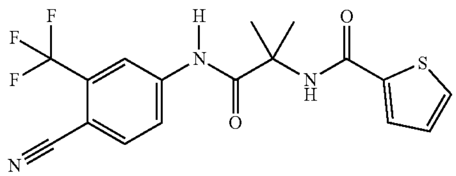 [SMILES: CC(C)(NC(=O)c1cccs1)C(=O)Nc1ccc(C#N)c(C(F)(F)F)c1] |
| 86 (page 41) | 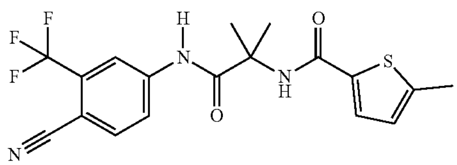 [SMILES: Cc1ccc(C(=O)NC(C)(C)C(=O)Nc2ccc(C#N)c(C(F)(F)F)c2)s1] |

Examples 53 and 86 of WO98/22432 have antiandrogenic activity and show a very low metabolic stability in human hepatocytes.

Inhibition of the human androgen receptor is associated with potential serious side effects such as loss of libido, erectile dysfunction, fatigue, osteoporosis and induced skeletal complications, hot flushes, altered body composition, arterial stiffness, new onset diabetes mellitus, cognitive decline, and increase cardiovascular morbidity and mortality (doi: 10.1016/j.eururo.2008.10.008).

Compounds of the present invention are generically encompassed by formula (I) of WO98/22432. The compounds of the present invention differ structurally from examples 53 and 86 of WO98/22432 (representing the closest analogues) in that they contain:
i) a phenyl ring which is substituted with one or two halogens in place of a 4-cyano-3-trifluoromethyl-phenyl group; and
ii) a 2-chloro-thiophene or a 2-bromo-thiophene moiety in place of an unsubstituted thiophene or a 2-methyl-thiophene moiety.

The structural differences unexpectedly result in potent IDO1 inhibition and in an increase in selectivity over the human androgen receptor whereas examples 53 and 86 of WO98/22432 show weaker IDO1 inhibition and do not show any or rather poor selectivity over the human androgen receptor. Additionally, the compounds of the present invention have been found to be metabolically stable in human hepatocytes (Table 3c).

The objective technical problem is thus to provide potent, selective, metabolically stable, and brain penetrating IDO1 inhibitors.

According to the present invention, the compounds disclosed herein have surprisingly been found to be potent, selective, metabolically stable, and brain penetrating IDO1 inhibitors.

Due to their potent inhibition of IDO1, increased selectivity over the human androgen receptor and metabolic stability in human hepatocytes, compounds of the present invention are expected to be both efficacious in vivo for the treatment of diseases and conditions of CNS origin and to have an acceptable window between efficacy and undesired effects such as loss of libido, erectile dysfunction, fatigue, osteoporosis and induced skeletal complications, hot flushes, altered body composition, arterial stiffness, new onset diabetes mellitus, cognitive decline, and increase cardiovascular morbidity and mortality.

Consequently, compounds of the present invention must be more viable for human use.

WO2005/111029 discloses compounds of formula (I) that are inhibitors of human Factor Xa being useful as antithrombotic agents.

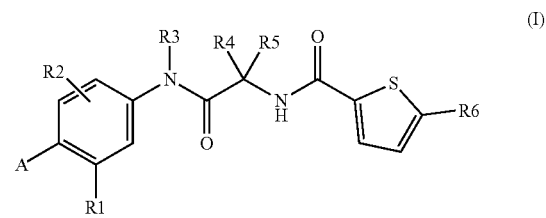

Formula (I) encompasses the specific examples 8 and 28, which exhibit a heterocyclic amide moiety A (Table 2).

TABLE 2

Examples 8 and 28 of WO2005/111029 exhibiting a heterocyclic amide moiety A within formula (I).

| Example no. in WO2005/111029 | Structure |
|---|---|
| 8 (page 175) | 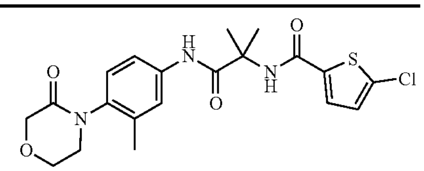 |
| 28 (page 200) | 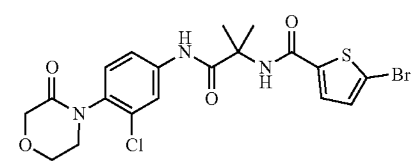 [SMILES: CC(C)(NC(=O)c1ccc(Br)s1)C(=O)Nc1ccc(N2CCOCC2=O)c(Cl)c1] |

Examples 8 and 28 of WO2005/111029 inhibit the human Factor Xa enzyme and show a high efflux.

Inhibition of the human Factor Xa enzyme is associated with undesired serious side effects such as extended bleeding. Currently available Factor Xa inhibitor medications (such as Rivaroxaban and Apixaban) are used as antithrombotic agents to prevent deep vein thrombosis, pulmonary emboli, and blood clots in atrial fibrillation. For a fast reversal of the effect an antidote has been developed (andexanet alfa). Additional use of Factor Xa inhibitors may include CNS indications such as neurodegeneration.

The compounds of the present invention differ structurally from formula (I) of WO2005/111029 in that they contain a phenyl ring which is substituted with one or two halogens in place of a phenyl ring which is substituted with a heterocyclic amide moiety A.

The structural difference unexpectedly results in an increase in selectivity over the human Factor Xa enzyme and in a low efflux ratio in the MDCK-MDR1 cell assay whereas examples 8 and 28 of WO2005/111029 inhibit the human Factor Xa enzyme and show a high efflux ratio (Table 4).

The objective technical problem is thus to provide potent, selective, metabolically stable, and brain penetrating IDO1 inhibitors.

According to the present invention, the compounds disclosed herein have surprisingly been found to be potent, selective, metabolically stable, and brain penetrating IDO1 inhibitors.

Due to their potent inhibition of IDO1, increased selectivity over the human Factor Xa enzyme and low in vitro efflux, compounds of the present invention are expected to show favorable brain penetration, which is required for efficacious drugs targeting the brain, and to have an acceptable window between efficacy and undesired serious side effects such as extended bleeding.

Consequently, compounds of the present invention must be more viable for human use.

WO2005/111013 discloses compounds of formula (I) that are inhibitors of human Factor Xa being useful as antithrombotic agents.

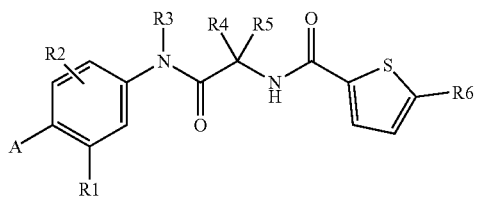

Formula (I) encompasses the specific example 22, which exhibits a heterocyclic moiety A within formula (I).

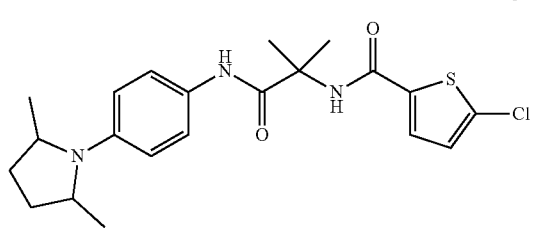

Example 22

(page 154)

Example 22 of WO2005/111013 inhibits the human Factor Xa enzyme and shows a medium metabolic stability in human hepatocytes.

Inhibition of the human Factor Xa enzyme is associated with undesired serious side effects such as extended bleeding. Currently available Factor Xa inhibitor medications (such as Rivaroxaban and Apixaban) are used as antithrombotic agents to prevent deep vein thrombosis, pulmonary emboli, and blood clots in atrial fibrillation. For a fast reversal of the effect an antidote has been developed (andexanet alfa). Additional use of Factor Xa inhibitors may include CNS indications such as neurodegeneration.

The compounds of the present invention differ structurally from formula (I) of WO2005/111013 in that they contain a phenyl ring which is substituted with one or two halogens in place of a phenyl ring which is substituted with a saturated heterocyclic moiety A.

The structural difference unexpectedly results in potent IDO1 inhibition and in an increase in selectivity over the human Factor Xa enzyme and in an increase in metabolic stability in human hepatocytes whereas example 22 of WO2005/111013 inhibits the human Factor Xa enzyme and shows a medium metabolic stability in human hepatocytes (Table 5).

The objective technical problem is thus to provide potent, selective, metabolically stable, and brain penetrating IDO1 inhibitors.

According to the present invention, the compounds disclosed herein have surprisingly been found to be potent, selective, metabolically stable, and brain penetrating IDO1 inhibitors.

Due to their potent inhibition of IDO1, increased selectivity over the human Factor Xa enzyme and increased metabolic stability in human hepatocytes, compounds of the present invention are expected to be efficacious in vivo for the treatment of diseases and conditions of CNS origin and to have an acceptable window between efficacy and undesired serious side effects such as extended bleeding.

Consequently, compounds of the present invention must be more viable for human use.

WO2005/111014 discloses compounds of formula (I) that are inhibitors of human Factor Xa being useful as antithrombotic agents.

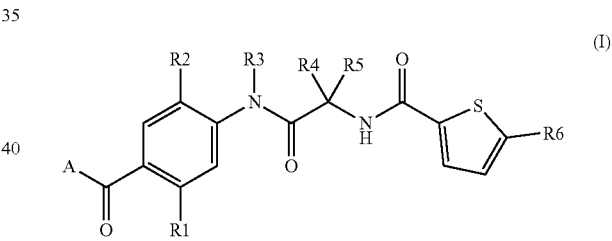

Formula (I) encompasses the specific example 4, which exhibits an amide moiety within formula (I).

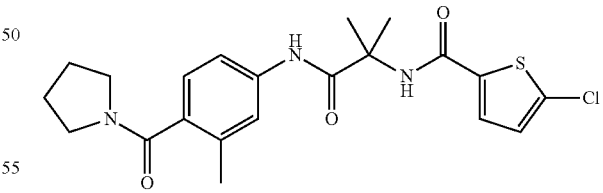

Example 4 (Page 137)

Example 4 of WO2005/111014 inhibits the human Factor Xa enzyme and shows a high efflux.

Inhibition of the human Factor Xa enzyme is associated with undesired serious side effects such as extended bleeding. Currently available Factor Xa inhibitor medications (such as Rivaroxaban and Apixaban) are used as antithrombotic agents to prevent deep vein thrombosis, pulmonary emboli, and blood clots in atrial fibrillation. For a fast reversal of the effect an antidote has been developed (andexanet alfa). Additional use of Factor Xa inhibitors may include CNS indications such as neurodegeneration.

The compounds of the present invention differ structurally from formula (I) of WO2005/111014 in that they contain a phenyl ring which is substituted with one or two halogens in place of a phenyl ring which is para-substituted with an amide moiety.

The structural difference unexpectedly results in an increase in selectivity of IDO1 inhibition over the human Factor Xa enzyme and in a low efflux ratio in the MDCK-MDR1 cell assay whereas example 4 of WO2005/111014 inhibits the human Factor Xa enzyme and shows a high efflux (Table 6).

The objective technical problem is thus to provide potent, selective, metabolically stable, and brain penetrating IDO1 inhibitors.

According to the present invention, the compounds disclosed herein have surprisingly been found to be potent, selective, metabolically stable, and brain penetrating IDO1. Due to their potent inhibition of IDO1, increased selectivity over the human Factor Xa enzyme and low in vitro efflux, compounds of the present invention are expected to show favorable brain penetration, which is required for efficacious drugs targeting the brain, and to have an acceptable window between efficacy and undesired serious side effects such as extended bleeding.

Consequently, compounds of the present invention must be more viable for human use.

None of the Factor Xa enzyme inhibitors described above teach or suggest the compounds of the present invention or their advantageous properties as inhibitors of IDO1 described herein.

DETAILED DESCRIPTION OF THE INVENTION

The compounds of the present invention are metabolically stable in human hepatocytes (see Tables 3b, 3c and 5 for metabolic stability). Therefore, compounds of the present invention are expected to have a favorable in vivo clearance and thus the desired duration of action in humans.

Stability in human hepatocytes refers to the susceptibility of compounds to biotransformation in the context of selecting and/or designing drugs with favorable pharmacokinetic properties. The primary side of metabolism for many drugs is the liver. Human hepatocytes contain the cytochrome P450 (CYPs) and additional enzymes for phase II metabolism (e.g. phosphatases and sulfatases), and thus represent a model system for studying drug metabolism in vitro. Enhanced stability in hepatocytes is associated with several advantages, including increase bioavailability and adequate half-life, which can allow lower and less frequent dosing in patients. Thus, enhanced stability in hepatocytes is a favorable characteristic for compounds that are to be used as drugs.

The compounds of the present invention show good membrane permeability and low to moderate in vitro efflux (see Tables 4 and 6 for MDCK assay MDR1 (P-gp)).

Therefore, compounds of the present invention are expected to show a favorable brain penetration which is required for efficacious CNS medicaments.

The MDCK assays provide information on the potential of a compound to pass the blood brain barrier. Permeability measurements across polarized, confluent MDCK-MDR1 cell monolayers grown on permeable filter supports are used as an in vitro absorption model: apparent permeability coefficients (PE) of the compounds across the MDCK-MDR1 cell monolayers are measured (pH 7.4, 37° C.) in apical-to-basal (AB) and basal-to-apical (BA) transport direction. The AB permeability (PEAB) represents drug absorption from the blood into the brain and the BA permeability (PEBA) drug efflux from the brain back into the blood via both, passive permeability as well as active transport mechanisms mediated by efflux and uptake transporters that are expressed on the MDCK-MDR1 cells, predominantly by the overexpressed human MDR1. Identical or similar permeabilities in both transport directions indicate passive permeation, vectorial permeability points to additional active transport mechanisms. Higher PEBA than PEAB (PEBA/PEAB >3) indicates the involvement of active efflux mediated by MDR1, which might compromise the goal to achieve sufficient brain exposure.

Therefore, this assay provides valuable support for selection of compounds applicable for further in vivo testing. High permeability not limited by efflux at the blood brain barrier is a favorable characteristic for compounds that are to be used for drugs acting primarily in the CNS. Consequently, to ensure high permeability at the blood brain barrier, it is highly preferred to minimize the efflux (efflux <3) at MDR1 transporter.

The compounds of the present invention show favorable pharmacokinetic properties in vivo as indicated by plasma and brain exposure after oral application in rats or mice.

In order to estimate the amount of administered drug to enter the brain, the brain to plasma ratio is used as surrogate parameter. As efflux transporters (e.g. P-gp) are located at the blood-brain barrier, compounds acting as substrates will be actively transported out of the brain. As these efflux transporters are not expressed in muscle tissue, the relative distribution ratio of compound between muscle and brain tissue can be used as indication for an efflux in vivo in rats or mice. In case there is no in vivo efflux detectable (in rats/mice) and in case there is no efflux in vitro (MDCK-MDR1 (P-gp)), a brain exposure in patients can be expected [see Table 7 for comparison of in vitro efflux data (MDCK-MDR1 assay) and in vivo efflux data (tissue distribution in rat/mouse after oral application)].

The present invention provides novel 2-[thiophen-2-yl)formamido]-N-(phenyl)-2-methylpropanamides of formula A

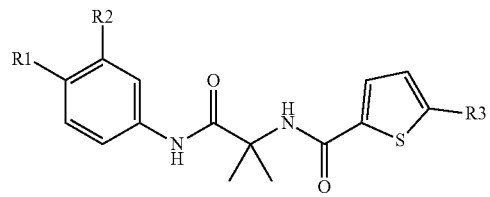

in which
R$^1$ represents chloro or bromo;
R$^2$ represents hydrogen or fluoro;
R$^3$ represents chloro or bromo;
or a salt thereof, particularly a pharmaceutically acceptable salt thereof.

The present invention provides novel 2-[thiophen-2-yl)formamido]-N-(phenyl)-2-methylpropanamides of formula A that unexpectedly are potent IDO1 inhibitors.

Another aspect of the invention refers to compounds according to formula A as potent and selective IDO1 inhibitors.

Another aspect of the invention refers to compounds according to formula A as potent IDO1 inhibitors having appropriate selectivity over the human androgen receptor.

Another aspect of the invention refers to compounds according to formula A as potent IDO1 inhibitors having appropriate selectivity over the human Factor Xa enzyme.

Another aspect of the invention refers to compounds according to formula A as potent and selective IDO1 inhibitors having appropriate membrane permeability and low in vitro efflux.

Another aspect of the invention refers to compounds according to formula A as potent and selective IDO1 inhibitors having high metabolic stability in human hepatocytes.

Another aspect of the invention refers to compounds according to formula A as potent and selective IDO1 inhibitors having appropriate membrane permeability, low in vitro efflux and high metabolic stability in human hepatocytes.

Another aspect of the invention refers to compounds according to formula A as potent, selective, and brain penetrating IDO1 inhibitors.

Another aspect of the invention refers to compounds according to formula A as potent, selective, metabolically stable, and brain penetrating IDO1 inhibitors.

Another aspect of the invention refers to pharmaceutical compositions, containing at least one compound according to formula A optionally together with one or more inert carriers and/or diluents.

A further aspect of the present invention refers to compounds according to formula A, for the use in the prevention and/or treatment of disorders associated with IDO1 inhibition.

Another aspect of the invention refers to processes of manufacture of the compounds of the present invention.

Preparation

The following schemes shall illustrate generally how to manufacture the compounds according to formula A and the corresponding intermediate compounds by way of example. The abbreviated substituents may be as defined above if not defined otherwise within the context of the schemes.

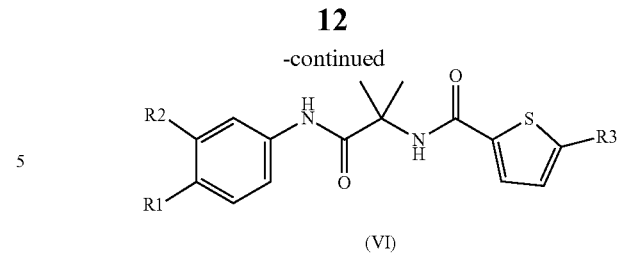

(VI)

Starting from commercially available compounds (I), in which PGA is a suitable protecting group forming an alkyl- or aryl ester (PGA is selected from the group consisting of methyl, ethyl, n-butyl, phenyl, p-nitrophenyl), compounds (III) can be obtained by reaction with an activated compound (II) (G represents halogen or uronium moieties such as chlorine, bromine, O-(benzotriazol-1-yl)-N,N,N',N'-tetramethyluronium or O-(7-azabenzotriazol-1-yl)-N,N,N',N'-tetramethyluronium) in a solvent such as tetrahyrofuran, 2-methyltetrahydrofuran, 1,4-dioxane or toluene in the presence of an organic base such as triethylamine, N-ethyl-diisopropylamine or N-methylmorpholine at temperatures ranging from −50° C. to 120° C.

Hydrolysis of compounds (III) is conducted with an inorganic base such as lithium hydroxide, sodium hydroxide or potassium hydroxide in a solvent or solvent mixture such as methanol, ethanol, tetrahydrofuran, 2-methyltetrahydrofuran or water at temperature ranging from −20° C. to 100° C. Activation of compounds (IV) with reagents such as O-(Benzotriazol-1-yl)-N,N,N',N'-tetramethyluronium tetrafluoroborate or O-(7-Azabenzotriazol-1-yl)-N,N,N',N'-tetramethyluronium-hexafluorophosphate in a solvent such as tetrahyrofuran, 2-methyltetrahydrofurane, 1,4-dioxane or toluene in the presence of an organic base such as triethylamine, N-ethyl-diisopropylamine or N-methylmorpholine at temperatures ranging from −50° C. to 120° C. is required before reaction with compounds (V) to obtain compounds (VI).

Scheme 1 Method A

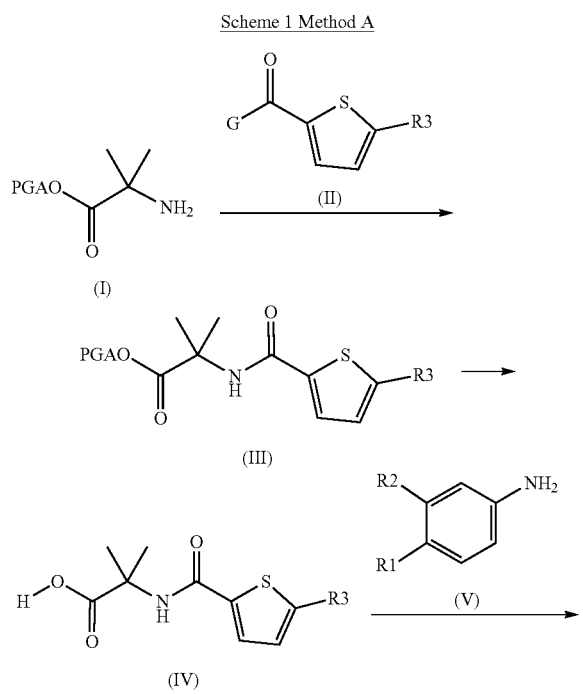

Scheme 2 Method B

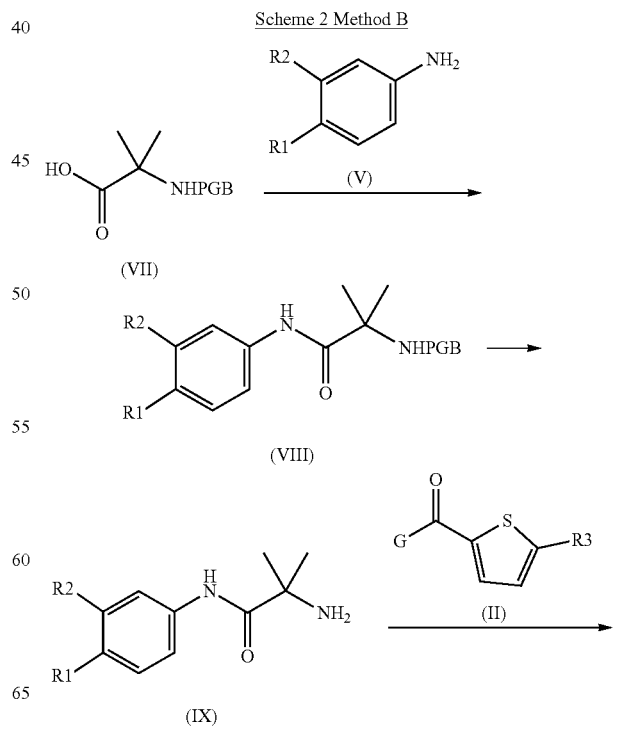

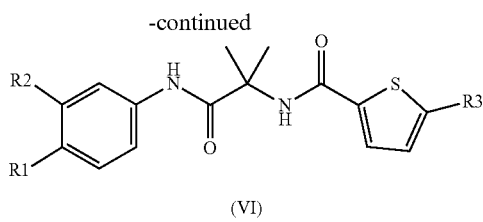

(VI)

Activation of commercially available compounds (VII) in which PGB is a suitable protecting group forming carbamates (PGB is selected from the group consisting of tert-butoxycarbonyl, benzyloxycarbonyl, allyloxycarbonyl or 9-fluorenylmethoxycarbonyl) with reagents such as O-(Benzotriazol-1-yl)-N,N,N',N'-tetramethyluronium tetrafluoroborate or O-(7-Azabenzotriazol-1-yl)-N,N,N',N'-tetramethyluronium-hexafluorophosphate in a solvent such as tetrahyrofuran, 2-methyltetrahydrofurane, 1,4-dioxane or toluene in the presence of an organic base such as triethylamine, N-ethyl-diisopropylamine or N-methylmorpholine at temperatures ranging from −50° C. to 120° C. is required prior to addition of compounds (V) in order to obtain compounds (VIII).

Removal of the protecting group with acids such as hydrogen chloride, hydrogen bromide, acetic acid or trifluoroacetic acid or organic bases such as triethylamine, N-ethyl-diisopropylamine or N-methylmorpholine in solvents such as dichloromethane, tetrahydrofuran, 1,4-dioxane or water at temperatures ranging from 0° C. to 100° C. results in the formation of compounds (IX).

Reaction of compounds (IX) with an activated compound (II) (G represents halogen or uronium moieties such as chlorine, bromine, O-(benzotriazol-1-yl)-N,N,N',N'-tetramethyluronium or O-(7-azabenzotriazol-1-yl)-N,N,N',N'-tetramethyluronium) in a solvent such as tetrahyrofuran, 2-methyltetrahydrofurane, 1,4-dioxane or toluene in the presence of an organic base such as triethylamine, N-ethyl-diisopropylamine or N-methylmorpholine at temperatures ranging from −50° C. to 120° C. is required to obtain compounds (VI).

In Schemes 1 and 2 all substituents $R^1$, $R^2$ and $R^3$ have the meaning as defined for formula A, the abbreviations PGA and PGB have the meaning of a protecting group, and the abbreviation G has the meaning of an activating group, all embodiments of the invention that directly refer thereto and specifically the meaning as defined in the claims.

General Definitions

Terms not specifically defined herein should be given the meanings that would be given to them by one skilled in the art in light of the disclosure and the context.

In case a compound of the present invention is depicted in form of a chemical name as well as a formula, the formula shall prevail in case of any discrepancy.

An asterisk may be used in sub-formulas to indicate the bond which is connected to the core molecule or to the substituent to which it is bound as defined.

The term "substituted" as used herein means that any one or more hydrogens on the designated atom is replaced with a selection from the indicated group, provided that the designated atom's viable valence number is not exceeded, and that the substitution results in a stable compound.

Stereochemistry:

Unless specifically indicated, throughout the specification and the appended claims, a given chemical formula or name shall encompass rotamers and tautomers, as well as mixtures in different proportions or mixtures of any of the foregoing forms where such isomers exist, as well as salts, including pharmaceutically acceptable salts thereof.

Salts:

The phrase "pharmaceutically acceptable" is employed herein to refer to those compounds, materials, compositions, and/or dosage forms which are, within the scope of sound medical judgment, suitable for use without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt or a complex with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid.

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like diethyl ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

BIOLOGICAL ASSAYS AND DATA

List of Abbreviations
BSA bovine serum albumin
cDNA complementary DNA
CSF cerebrospinal fluid
DMSO dimethyl sulfoxide
HEPES 2-(4-(2-hydroxyethyl)-1-piperazinyl)-ethane sulfonic acid
IFN interferone
$K_3$EDTA 1,2-diaminoethane-N,N,N',N'-tetra-acetic acid tripotassium salt
LPS lipopolysaccharide
MDCK Madin-Darby canine kidney
MDR1 Multi drug resistance protein 1
P-gp p-Glycoprotein
% QH % of liver blood flow
rpm rotation per minute
rt room temperature
U unit
WBA whole blood assay
xg times gravity The data provided for Assays A-F are the arithmetic means of the individual assay results ($IC_{50}$ values, % QH and efflux ratio) with the standard deviation, and with N as the number of available data points for the corresponding assay.

The biological activity of compounds is determined by the following methods:

Assay A. In Vitro Testing of IDO1 Potency:
Determination of In Vitro Pharmacological Activity This assay assesses the reduction of Kynurenin (enzymatic catabolite of L-Tryptophane) in an inhibitor dose response in human whole blood stimulated with LPS and IFN-gamma. Kynurenin is quantified against D4-Kynurenin (internal standard) via LC-MS/MS. The assay is used to determine specific IC50 and IC90 values for compounds in a human model.

Material and Reagents:
- Human whole blood from healthy donors, gained in blood sampling syringes with Li-Heparin anticoagulant (SARSTEDT Monovette, LH 9 mL, orange color code)
- 96 well plates (THERMO FISHER Abgene Storage Plate 96-well 0.8 mL, cat no AB0765)
- AirPore Tapes (QIAGEN)
- RPMI 1640 with GlutaMAX supplement (GIBCO, cat no 61870010)
- Lipopolysaccharides from *E. coli* dissolved in RPMI, sterile-filtered (SIGMA ALDRICH, cat no L3129-25MG, *E. coli* 0127:B8, Lot #016M4187V
- Recombinant human Interferon-gamma (PEPROTECH via TEBU-BIO, cat no 167300-02-B, Lot #121527) dissolved in 0.1% recombinant human serum albumin (SIGMA ALDRICH, cat no A6608-100MG, Lot #SLBQ1282V) in DPBS
- Acetonitrile, CHROMASOLV for HPLC (SIGMA ALDRICH, cat no 34851-2.5L)
- L-Kynurenin D4 (BUCHEM BV), 5 mM in DMSO
- DMSO
- Acetic Acid, 100% water free for analysis (MERCK, cat no 34885-2.5L)
- Methanol, CHROMASOLV, for HPLC (SIGMA-ALDRICH, cat no 1.00063.2500)

Procedure:
IFN-gamma and LPS were diluted in RPMI medium to reach the 8× concentrated desired assay concentration:
IFN-gamma 25 ng/mL×8 200 ng/mL
LPS 500 ng/mL×8 4 µg/mL
LPS was ultrasonicated for at least 10 minutes and vortexed directly before usage.

IFN-gamma was gently mixed by pipetting up and down.

A stimulants mixture was prepared by mixing both dilutions in a 1:1 ratio which results in the 4× desired end concentration of each stimulant.

Compound dilutions in half logarithmic serial dilutions were prepared in 100% DMSO in a range between 4 mM and 4 µM. These dilutions were further diluted 1:100 in RPMI medium.

Assay plates were prepared with stimulants as well as with inhibitor titration curves (3 technical replicates, 4 biological replicates). All reagents are plated 4× concentrated in a volume of 60 µL per well. A positive control (no stimulation, no inhibitor treatment, basal activity) and a negative control (stimulation without inhibitor treatment, maximum signal) were included in each plate (6 technical replicates). All wells were topped-up to an end volume of 120 µL with RPMI medium before the whole blood samples were added.

Li-Heparin treated whole blood from 4 donors was received directly after blood drawing (<2 h). Each sample was diluted 1:2 with RPMI medium.

120 µL of the diluted blood samples were added to the designated plate wells which lead to an end volume of 240 µL, a 1× reagent concentration, a compound concentration range between 10 µM and 0.01 µM and 0.25% DMSO in each well.

Plates were sealed with air pore tapes and incubated for 24 h at 37° C., 5% CO2.

After incubation time assay plates were shaken shortly and then centrifuged to gain plasma: 15 min, 2000×g, rt.

200 µL of acetonitrile was pipetted in each well of fresh 96 well plates in which 100 µL of plasma that was aspirated from each assay sample was transferred. Plates were placed on a shaker for 5 min, 1000 rpm before cooling to −80° C. for 20 to 60 min for further precipitation.

Internal Standard solution was prepared: 5 mM D4-Kynurenin in DMSO was diluted 1:3333 in MilliQ water to a 1.5 µM solution. 100 µL of internal standard solution was added to each well, leading to a D4-Kynurenin end concentration of 0.375 µM in each well.

Plates were centrifuged to sediment the precipitate: 20 min, 2000×g, rt.

The supernatant was transferred into fresh 96 well plates in preparation for LC/MS analysis.

LC parameter
Cartridge(type & bed volume): C18 (12 µL)
Flow rate pump 1/2/3 in [mL/min]: 1.5/1.25/1.25
LC solvent pump 1/2/3: 0.5% Acetic Acid in double distilled H2O/0.5% Acetic
Acid in Methanol/0.5% Acetic Acid in Methanol
Wash solvent (wash 1/2): H2O/MeOH
LabView config file: ido.cfg
Aspiration time: 250 ms
Wash time: 3000 ms
Elute time: 3000 ms
Equilibration time: 500 ms
Sip Height: 2 mm
MS parameter
Mass spectrometer: TSQ Vantage
Ion Source: HESI II
Spray Voltage: 2500V
Capillary Temperature: 325° C.
Sheath Gas pressure: 30 psi
Vaporizer Temperature: 500° C.
Aux Gas Pressure: 45 psi
Scan Width: 0.1 amu
Resolution: SRM (0.7/0.7)
MRM transition of analyte/internal standard in Dalton
L-Kynurenin 209.11 (mother structure)—94.10
D4-Kynurenin 213.05 (mother structure)—150.14
Results were given as ratio of L-Kynurenin/D4-Kynurenin.

Dose response curves were calculated and fitted as inhibition percentage of control between 100% (negative control) and 0% (positive control, unstimulated basal activity).

Assay B. In Vitro Testing of Androgen Receptor Potency:
Determination of In Vitro Pharmacological Activity The human androgen receptor (AR) assay was run using Product #IB03001 from Indigo Biosciences. The cell line provided in this kit carries a reporter gene, induced upon AR stimulation. This reporter gene is cDNA encoding for beetle luciferase, a 62 kD protein originating from the North American firefly (*Photinus pyralis*). This luciferase catalyzes the mono-oxidation of D-luciferin yielding oxyluciferin, adenosine monophosphate, pyrophosphate, CO2, and photon emission. The luminescence intensity of the reaction is quantified using a luminometer.

To run the assay, the cells are thawed by adding pre-warmed cell recovery medium to each tube, then placed in a 37° C. water bath. 30000 viable cells in 200 µl are plated (collagen coated plates) and incubated at 37° C., ≥85% humidity, 5% CO2 for 24 hours. Media is replaced with compound screening medium. Cells are then challenged with 125 pM (EC80) 6a-Fl Testosterone and compounds are applied in half logarithmic dilutions from 10 µM to 10 nM. Assay plates are then incubated at 37° C., ≥85% humidity, 5% CO2 for 22-24 hours. Media is replaced with luciferase detection reagent and allowed 5 minutes to equilibrate prior to luminescence quantification.

Data Analysis consisted of calculating percentage of control between 100% (Negative control:6a-Fl Testosterone) and 0 (positive control: no 6a-FL Testosterone). Fitting of normalized values was made 4-Parameter sigmoidal binding curve (Log[conc]) vs. signal.

Assay C. In Vitro Testing of Human Factor Xa Potency: Determination of In Vitro Pharmacological Activity Measurement of active human Factor Xa using a specific chromogenic substrate which is labeled with a p-nitroanilino group (pNA). The cleavage in between the binding of the peptide substrate and the pNA-group is followed by a color change, which can be detected at 405 nm. The amount of cleaved substrate is directly proportional to the amount of active Xa.

0.8 mg (100 U) human Factor Xa (Enzyme Research Laboratories; HFXa1011) were solved in 0.444 ml H2O (Millipore), which accords to a stock solution of 19.28 µM or 225 U/ml. Further dilutions were made in the assay buffer (Tris 100 mM, NaCL 150 mM, adjusted to a pH of 7.8 with HCL, containing 0.1% BSA and 0.05% Tween20). 25 mg (1 vial) of the chromogenic substrate S2765 (Chromogenix; S2765) was solved in 3.5 ml H2O (Millipore) to achieve a stock solution of 10 mM.

Compounds were solved and diluted in DMSO where the final dilution in the assay is 1:10 resulting in a final concentration of 1% DMSO.

or compounds solved in H2O were diluted in H2O
  the prefinal dilution step was 1:10 in the assay buffer containing 11% DMSO resulting in 10% DMSO
  final dilution in the assay is 1:10 resulting in a final concentration of 1% DMSO Compounds were tested at final concentrations of 10 µM to 0.003 nM or lower. 5 µl human factor Xa (final concentration 0.86 nM), 2 µl compound dilution or assay buffer (containing 10% DMSO) and 8 µl assay buffer were pipetted in triplicates into a 384-well plate and incubated in the Thermomix at 24° C. for 10 minutes.

After addition of 5 µl chromogenic substrate (final concentration 0.5 mM) the enzyme-substrate reaction started and the kinetic measurement with the SpectraMax Monochromator was started within 1-2 minutes.

Parameter of measurement: (Spectra ax, Monochromator)
Absorbance; 1.LM 405 nM
Kinetic: 16 min each 2nd minute (9 times)
Negative Control (NC) 5 µl human factor Xa+10 µl assay buffer+5 µl Substrate
Positive Control (PC): 5 µl human factor Xa+2 µl Nafamostat (commercially available, final concentration: 1 µM)+8 µl assay buffer+5 µl Substrate
Blank (optional): 15 µl assay buffer+5 µl Substrate
Calculation of IC50, KI and the % effect at the highest concentration (Ratio)
For the calculation the average of the Vmax-values in between 120 sec to 720 sec were taken.

A x/y-Plot was created: x=log (M, Compound); y=vmax (drfu/min)

The data were analyzed with the curve fitting model: log (inhibitor) vs. response—Variable slope (four parameters)

The results of this fit were Top, Bottom, Log (IC50, M), Hillslope and IC50 (M)

Assay D. Assessment of Metabolic Stability in Human Hepatocytes

The metabolic degradation of the test compound is assayed in a hepatocyte suspension. After recovery from cryopreservation, human hepatocytes are incubated in Dulbecco's modified eagle medium supplemented with 3.5 µg glucagon/500 mL, 2.5 mg insulin/500 mL and 3.75 mg/500 mL hydrocortisone) containing 5% or 50% human serum or in absence of serum.

Following a 30 min preincubation in a cell culture incubator (37° C., 10% CO2), 5 µl of test compound solution (80 µM; derived from a 2 mM DMSO stock solution by dilution 1:25 with medium) are added into 395 µl hepatocyte suspension, resulting in a final cell density of 1 Mio cells/mL, a final test compound concentration of 1 µM, and a final DMSO concentration of 0.05%.

The cells are incubated for six hours (incubator, orbital shaker) and samples (25 µl) are removed from the incubation after 0, 0.5, 1, 2, 4 and 6 hours. Samples are transferred into acetonitrile and pelleted by centrifugation (5 min). The supernatant is transferred to a new 96-deepwell plate, evaporated under nitrogen and resuspended prior to analysis of decline of parent compound by HPLC-MS/MS.

CLint is calculated as follows:

$$CL\_INTRINSIC = k/CD \times 1000/60$$

k: slope of the regression line for parent decline [$h^{-1}$], CD: cell density of vital cells [10e6 cells/mL], The calculated in vitro hepatic intrinsic clearance is scaled up to the intrinsic in vivo hepatic Clearance and used to predict hepatic in vivo blood clearance (CL) by the use of a liver model (well stirred model):

$$CL\_INTRINSIC\_INVIVO \text{ [ml/min/kg]} = (CL\_INTRINSIC \text{ [µL/min/10}e6 \text{ cells]} \times \text{hepatocellularity [10}e6 \text{ cells/g liver]} \times \text{liver factor [g/kg bodyweight]})/1000$$

$$CL\text{[ml/min/kg]} = CL\_INTRINSIC\_INVIVO \text{ [ml/min/kg]} \times \text{hepatic blood flow [ml/min/kg]}/(CL\_INTRINSIC\_INVIVO\text{[ml/min/kg]} + \text{hepatic blood flow [ml/min/kg]})$$

Results are expressed as percentage of hepatic blood flow:

$$QH[\%] = CL\text{[ml/min/kg]}/\text{hepatic blood flow [ml/min/kg])}$$

Hepatocellularity, human: 120×10e6 cells/g liver
Liver factor, human: 25.7 g/kg bodyweight
Blood flow, human: 20.7 ml/(min×kg)

Assay E. MDCK assay MDR-1 (P-gp)

Apparent permeability coefficients ($P_{app}$) of the compounds across MDCK-MDR1 monolayers (MDCKII cells transfected with human MDR1 gene) are measured in apical-to-basal (AB) and basal-to-apical (BA) direction.

MDCK-MDR1 cells ($6\times10^5$ cells/cm$^2$) are seeded onto filter inserts (Corning, Transwell, polycarbonate, 0.4 µm pore size) and cultured for 9 to 10 days. Compounds dissolved in DMSO stock solution (1-20 mM) are diluted with HTP-4 buffer (128.13 mM NaCl, 5.36 mM KCl, 1 mM MgSO4, 1.8 mM CaCl$_2$, 4.17 mM NaHCO$_3$, 1.19 mM Na2HPO4, 0.41 mM NaH2PO4, 15 mM HEPES, 20 mM glucose, pH 7.4) supplemented with 0.25% BSA to prepare the transport solutions, resulting in a final test concentration of 1 µM or 10 µM and a final DMSO content of 0.5%. The transport solution is applied to the apical or basolateral donor side for measuring A-B or B-A permeability, respectively. The receiver side contains HTP-4 buffer supplemented with 0.25% BSA. Samples are collected at the start and end of experiment from the donor and at various time intervals for up to 2 hours from the receiver side for concentration measurement by HPLC-MS/MS. Sampled receiver volumes are replaced with fresh receiver solution.

All data reported for Assay E were measured with a final test concentration of 10 µM.

Assay F. Determination of Tissue Distribution in Rat/Mouse After Oral Application of Compounds Male Han Wistar rats or C57BL/6NRj mice were orally dosed with 10 µmol/kg of compound to be investigated, suspended in 0.5% Natrosol/0.015% Tween80. Blood was collected in $K_3$EDTA containing vials from the sublingual vein in short time Isoflurane anesthesia in rat or from the saphenous vein in conscious mice at 0.83, 0.25, 0.5, 1, 2, 3, 4, 8 and 24 hours post administration. Subsequently, plasma was prepared by centrifugation for 5 min at 5000 rpm and stored at −20° C.

Tissues and CSF were sampled in anaesthetized animals. CSF was collected from the cisterna *magna*. Following exsanguination a femoral muscle sample was collected. Cranium and the dura matter were removed and the complete brain was collected. Before transfer of the muscle and brain sample to pre-weight homogenization devices (Precellys®) the tissues were rinsed with saline and blotted dry.

For homogenization, four parts (v/w) homogenization buffer (37.5% acetonitrile, 37.5% methanol, 25% water) were added. Tissues were homogenized with a Precellys® Evolution homogenizer. Five µL of the homogenate were added to 70 µL of a 1 to 1 (v/v) mixture of acetonitrile and methanol and frozen for at least 10 min at −18° C.

For final sample preparation, the sample was centrifuged at 4000 rpm for 1 min, and an aliquot of the resulting supernatant (30 µL) was mixed with 170 µL formic acid prior to injection to LC-MS. Calibration curves were prepared accordingly in rat and mouse plasma, respectively. All animal care and experimental procedures at Boehringer Ingelheim were conducted in compliance with the German and European Animal Welfare Act (EU Directive 2010/63/EU) and were approved by the Regierungspräsidium Tübingen as the responsible local German authority (reference number 35/9185.81-8/14-009-G).

The compounds of the present invention have surprisingly been found to be potent, selective, metabolically stable, and brain penetrating IDO1 inhibitors (selective over the human Factor Xa, and no in vitro efflux) whereas example 5-ethynyl-N-{1-trifluoromethyl-1-[3-methyl-4-(3-oxomorpholin-4-yl)phenylcarbamoyl]ethyl}thiophene-2-carboxamide of WO2006/034822 (page 91, lines 7-8, 5-Ethinyl-thiophen-2-carbonsäure-N-{1-trifluormethyl-1-[3-methyl-4-(3-oxo-morpholin-4-yl)-phenylcarbamoyl]-ethyl}-amid) is a potent human Factor Xa inhibitor showing a high efflux ratio which might compromise the goal to achieve sufficient brain exposure (see Table 3a).

For the compounds of the invention a high selectivity over the human Factor Xa enzyme (i.e. potent IDO1 inhibition showing low IC50 values in Assay A, and low inhibition of the human Factor Xa enzyme (showing high IC50 values in Assay C) and a low efflux ratio (efflux <3 in Assay E) is desired, i.e. the compounds of the present invention are potent, selective, metabolically stable, and brain penetrating IDO1 inhibitors.

TABLE 3a

Comparison of biological data of the compounds of the present invention with the prior art compounds in WO2006/034822

| Example | IC50 Factor Xa Assay C | IC50 IDO1 Human Whole Blood Assay A | Selectivity Assay C/ Assay A | Efflux ratio Assay E |
|---|---|---|---|---|
| WO2006/034822 5-Ethinyl-thiophen-2-carbonsäure-N-{1-trifluormethyl-1-[3-methyl-4-(3-oxo-morpholin-4-yl)-phenylcarbamoyl]-ethyl}-amid (page 91, lines 7-8) | 48 nM | 601 +− 249 nM (N = 4) | 0.08 | 32 (N = 1) |
| 1 | >10000 nM | 173 +− 68 nM (N = 10) | >57 | 0.6 +− 0.1 (N = 4) |
| 2 | >10000 nM | 192 +− 125 nM (N = 11) | >52 | 0.7 +− 0.4 (N = 4) |
| 3 | >10000 nM | 183 +− 178 nM (N = 12) | >55 | 0.4 +− 0.1 (N = 4) |
| 4 | >10000 nM | 240 +− 94 nM (N = 12) | >42 | 0.5 +− 0.1 (N = 4) |
| 5 | >10000 nM | 173 +− 108 nM (N = 8) | >57 | 0.7 +− 0.2 (N = 4) |

The compounds of the present invention have surprisingly been found to be potent, metabolically stable, and brain penetrating IDO1 inhibitors (no in vitro efflux) whereas examples 4,6 and 159 of WO2007/003536 exhibit either low metabolic stability or a high in vitro efflux ratio which might compromise the goal to achieve sufficient brain exposure (see Table 3b). The specific examples 4,6 and 159 of WO2007/003536 show a substantial in vivo efflux (Assay F, for data see Table 7) after oral application of these compounds in rats.

For the compounds of the invention a high stability in human hepatocytes (low % QH values in Assay D) and/or a low efflux ratio (efflux <3 in Assay E and F) is desired, i.e. the compounds of the present invention are potent, selective, metabolically stable, and brain penetrating IDO1 inhibitors.

TABLE 3b

Comparison of biological data of the compounds of the present invention with the prior art compounds in WO2007/003536

| Example | IC50 Factor Xa Assay C | IC50 IDO1 Human Whole Blood Assay A | Selectivity Assay C/ Assay A | Hepatocyte stability Assay D | Efflux ratio Assay E |
|---|---|---|---|---|---|
| WO2007/ 003536 Ex. 4 | >10000 nM | 57 +− 13 nM (N = 4) | >175 | 50.7 +− 4.4 (N = 17) | 1.0 +− 0.13 (N = 4) |
| WO2007/ 003536 Ex. 6 | >10000 nM | 61 +− 21 nM (N = 4) | >164 | 15.4 +− 3.5 (N = 19) | 7.6 +− 1.4 (N = 4) |

TABLE 3b-continued

Comparison of biological data of the compounds of the present
invention with the prior art compounds in WO2007/003536

| Example | IC50 Factor Xa Assay C | IC50 IDO1 Human Whole Blood Assay A | Selectivity Assay C/ Assay A | Hepatocyte stability Assay D | Efflux ratio Assay E |
|---|---|---|---|---|---|
| WO2007/ 003536 Ex. 159 | >10000 nM | 793 +− 385 nM (N = 4) | >13 | 25.5 +− 2.4 (N = 19) | 1.8 +− 0.54 (N = 3) |
| 1 | >10000 nM | 173 +− 68 nM (N = 10) | >57 | <4.1 (N = 3) | 0.6 +− 0.1 (N = 4) |
| 2 | >10000 nM | 192 +− 125 nM (N = 11) | >52 | <4.1 (N = 3) | 0.7 +− 0.4 (N = 4) |
| 3 | >10000 nM | 183 +− 178 nM (N = 12) | >55 | 6.8 +− 2.8 (N = 3) | 0.4 +− 0.1 (N = 4) |
| 4 | >10000 nM | 240 +− 94 nM (N = 12) | >42 | 6.4 +− 3.1 (N = 3) | 0.5 +− 0.1 (N = 4) |
| 5 | >10000 nM | 173 +− 108 nM (N = 8) | >57 | 4.8 +− 1.0 (N = 3) | 0.7 +− 0.2 (N = 4) |

The compounds of the present invention have surprisingly been found to be potent IDO1 inhibitors and to be selective over the human androgen receptor, whereas examples 53 and 86 of WO98/22432 inhibit the human androgen receptor and show weaker IDO1 inhibition and therefore do not show any or rather poor selectivity over the human androgen receptor (see Table 3c). Additionally, the compounds of the present invention show enhanced metabolic stability (low % QH value) in the human hepatocyte assay, whereas examples 53 and 86 of WO98/22432 show a very low metabolic stability in human hepatocytes (see Table 3c). Therefore, the compounds of the present invention have surprisingly been found to be potent, selective, metabolically stable, and brain penetrating IDO1 inhibitors.

For the compounds of the invention a high selectivity over the human androgen receptor (i.e. potent IDO1 inhibition showing low IC50 values in Assay A, and low inhibition of the human androgen receptor showing high IC50 values in Assay B) and high stability in human hepatocytes (low % QH values in Assay D) is desired, i.e. the compounds of the present invention are potent, selective, metabolically stable, and brain penetrating IDO1 inhibitors.

The compounds of the present invention have surprisingly been found to be potent, selective, metabolically stable, and brain penetrating IDO1 inhibitors (selective over the human Factor Xa, and no in vitro efflux) whereas examples 8 and 28 of WO2005/111029 are potent human Factor Xa inhibitors showing a high efflux ratio which might compromise the goal to achieve sufficient brain exposure (see Table 4).

For the compounds of the invention a high selectivity over the human Factor Xa enzyme (i.e. potent IDO1 inhibition showing low IC50 values in Assay A, and low inhibition of the human Factor Xa enzyme showing high IC50 values in Assay C) and a low efflux ratio (efflux <3 in Assay E) is desired, i.e. the compounds of the present invention are potent, selective, metabolically stable, and brain penetrating IDO1 inhibitors.

TABLE 3c

Comparison of biological data of the compounds of the present
invention with the prior art compounds in WO98/22432

| Ex | IC50 Human Androgen Receptor Assay B | IC50 IDO1 Human Whole Blood Assay A | Selectivity Assay B/ Assay A | Hepatocyte stability Assay D |
|---|---|---|---|---|
| WO98/22432 example 53 (page 38) | 1057 +− 353 nM (N = 3) | 1571 +− 601 nM (N = 4) | 0.7 | 93.4 +− 1.8 (N = 4) |
| WO98/22432 example 86 (page 41) | 2410 +− 88 nM (N = 3) | 493 +− 201 nM (N = 4) | 4.9 | 93.5 +− 1.0 (N = 4) |
| 1 | 7463 +− 657 nM (N = 2) | 173 +− 68 nM (N = 10) | 43 | <4.1 (n = 3) |
| 2 | >10000 nM (N = 3) | 192 +− 125 nM (N = 11) | >52 | <4.1 (N = 3) |
| 3 | 6039 +− 859 nM (N = 3) | 183 +− 178 nM (N = 12) | 33 | 6.8 +− 2.8 (N = 3) |
| 4 | >10000 nM (N = 3) | 240 +− 94 nM (N = 12) | >42 | 6.4 +− 3.1 (N = 3) |
| 5 | >10000 nM (N = 3) | 173 +− 108 nM (N = 8) | >58 | 4.8 +− 1.0 (N = 3) |

TABLE 4

Comparison of biological data of the compounds of the present invention with the prior art compounds in WO2005/111029

| Example | IC50 Factor Xa Assay C | IC50 IDO1 Human Whole Blood Assay A | Selectivity Assay C/ Assay A | Efflux ratio Assay E |
|---|---|---|---|---|
| WO2005/ 111029 Ex. 8 | 40 nM | 4659 +− 2555 nM (N = 4) | 0.01 | 26.8 +− 12.5 (N = 3) |
| WO2005/ 111029 Ex. 28 | 26 nM | 231 +− 100 nM (N = 4) | 0.11 | 19.5 +− 12.3 (N = 3) |
| 1 | >10000 nM | 173 +− 68 nM (N = 10) | >57 | 0.6 +− 0.1 (N = 4) |
| 2 | >10000 nM | 192 +− 125 nM (N = 11) | >52 | 0.7 +− 0.4 (N = 4) |
| 3 | >10000 nM | 183 +− 178 nM (N = 12) | >55 | 0.4 +− 0.1 (N = 4) |
| 4 | >10000 nM | 240 +− 94 nM (N = 12) | >42 | 0.5 +− 0.1 (N = 4) |
| 5 | >10000 nM | 173 +− 108 nM (N = 8) | >57 | 0.7 +− 0.2 (N = 4) |

The compounds of the present invention have surprisingly been found to be potent, selective, metabolically stable, and brain penetrating IDO1 inhibitors (selective over the human Factor Xa, and metabolically stabile in human hepatocytes) whereas example 22 of WO2005/111013 inhibits the human Factor Xa enzyme and shows a medium metabolic stability in human hepatocytes (see Table 5).

For the compounds of the invention a high selectivity over the human Factor Xa enzyme (i.e. potent IDO1 inhibition showing low IC50 values in Assay A, and low inhibition of the human Factor Xa enzyme showing high IC50 values in Assay C) and high stability in human hepatocytes (low % QH values in Assay D) is desired, i.e. the compounds of the present invention are potent, selective, metabolically stable, and brain penetrating IDO1 inhibitors.

TABLE 5

Comparison of biological data of the compounds of the present invention with the prior art compounds in WO2005/111013

| Example | IC50 Factor Xa Assay C | IC50 IDO1 Human Whole Blood Assay A | Selectivity Assay C/ Assay A | Hepatocyte stability Assay D |
|---|---|---|---|---|
| WO2005/ 111013 Ex. 22 | 429 nM | 1151 +− 608 nM (N = 3) | 0.37 | 55.7 +− 21.4 (N = 3) |
| 1 | >10000 nM | 173 +− 68 nM (N = 10) | >57 | <4.1 (N = 3) |
| 2 | >10000 nM | 192 +− 125 nM (N = 11) | >52 | <4.1 (N = 3) |
| 3 | >10000 nM | 183 +− 178 nM (N = 12) | >55 | 6.8 +− 2.8 (N = 3) |
| 4 | >10000 nM | 240 +− 94 nM (N = 12) | >42 | 6.4 +− 3.1 (N = 3) |
| 5 | >10000 nM | 173 +− 108 nM (N = 8) | >57 | 4.8 +− 1.0 (N = 3) |

The compounds of the present invention have surprisingly been found to be potent, selective, metabolically stable, and brain penetrating IDO1 inhibitors (selective over the human Factor Xa, and no in vitro efflux) whereas example 4 of WO2005/111014 is a potent human Factor Xa inhibitors showing a high efflux ratio which might compromise the goal to achieve sufficient brain exposure (see Table 6).

For the compounds of the invention a high selectivity over the human Factor Xa enzyme (i.e. potent IDO1 inhibition showing low IC50 values in Assay A, and low inhibition of the human Factor Xa enzyme showing high IC50 values in Assay C) and a low efflux ratio (efflux <3 in Assay E) is desired, i.e. the compounds of the present invention are potent, selective, metabolically stable, and brain penetrating IDO1 inhibitors.

TABLE 6

Comparison of biological data of the compounds of the present invention with the prior art compounds in WO2005/111014

| Example | IC50 Factor Xa Assay C | IC50 IDO1 Human Whole Blood Assay A | Selectivity Assay C/ Assay A | Efflux ratio Assay E |
|---|---|---|---|---|
| WO2005/ 111014 Ex. 4 (page 139) | 8 nM | 338 +− 313 nM (N = 10) | 0.03 | 5.7 |
| 1 | >10000 nM | 173 +− 68 nM (N = 10) | >57 | 0.6 +− 0.1 (N = 4) |
| 2 | >10000 nM | 192 +− 125 nM (N = 11) | >52 | 0.7 +− 0.4 (N = 4) |
| 3 | >10000 nM | 183 +− 178 nM (N = 12) | >55 | 0.4 +− 0.1 (N = 4) |
| 4 | >10000 nM | 240 +− 94 nM (N = 12) | >42 | 0.5 +− 0.1 (N = 4) |
| 5 | >10000 nM | 173 +− 108 nM (N = 8) | >57 | 0.7 +− 0.2 (N = 4) |

The compounds of the present invention have surprisingly been found to show favorable pharmacokinetic properties in vivo as indicated by plasma and brain exposure after oral application in rats or mice. Examples 3 and 4 have surprisingly been found to be potent and selective IDO1 inhibitors (selective over the human androgen receptor and the human Factor Xa), to be metabolically stable and to show neither in vitro nor in vivo efflux (Tables 3a-7). Therefore, brain exposure in patients can be expected which is required for substantial inhibition of IDO1 in the brain over 24 h.

In contrast, the specific examples 4, 6 and 159 of WO2007/003536 show a substantial in vivo efflux in the same assay (Assay F, for data see Table 7) after oral application of these compounds in rats.

TABLE 7

Comparison of in vitro efflux data (MDCK-MDR1 assay) and in vivo efflux data (tissue distribution in rat/mouse after oral application) of the compounds of the present invention with the prior art compounds in WO2007/003536

| Example | MDCK-MDR1 efflux ratio (Assay E) | in vivo efflux (Assay F) |
|---|---|---|
| WO2007/003536 Ex. 4 | 1.0 | 3.3 (rat) |
| WO2007/003536 Ex. 6 | 7.6 | 12.6 (rat) |
| WO2007/003536 Ex. 159 | 1.8 | 6.2 (rat) |
| 3 | 0.50 | 0.60 (mouse) |
| 4 | 0.50 | 0.50 (rat) |

The present invention provides compounds according to formula A that unexpectedly are potent, selective, metabolically stable, and brain penetrating IDO1 inhibitors, i.e. the compounds show high potency for the human IDO1 enzyme, high selectivity over the human androgen receptor and human Factor Xa enzyme, high metabolic stability in human hepatocytes and neither in vitro (MDCK-MDR1 assay) nor in vivo efflux (indicated by muscle/brain tissue distribution in rat/mouse).

Full efficacy in patients, i.e. >90% inhibition of the IDO1 enzymatic activity, is associated with trough plasma concentrations corresponding to the in vitro $IC_{50}$ value for IDO1 inhibition determined in the human whole blood assay (DOI: 10.1002/jcph.855, DOI: 10.1158/1078-0432.CCR-16-2272). In clinical indications involving the central nervous system (CNS), a brain concentration equal to the trough plasma concentration has to be maintained over 24 h in the brain to be useful in the treatment of diseases and conditions wherein IDO1 inhibition is of therapeutic benefit. However, the efficacious compound plasma exposure needs to be free of undesired side effects. In order to account for variability between patients, higher plasma compound exposures have to be devoid of side effects. The ratio between the efficacious compound plasma exposure and the plasma exposure, at which the first side effects occur, is defined as safety window.

The safety window is substantially reduced by:
(i) low potency, as high plasma levels would be required to achieve efficacy, which might also result in a higher risk for undesired side effects,
(ii) low selectivity over targets such as the human androgen receptor or human Factor Xa, since side effects might be caused by off-target affinity,
(iii) low metabolic stability, since a high initial compound plasma exposure would be required to assure CNS levels which provide substantial inhibition over 24 h,
(iv) a high efflux ratio at the blood brain barrier (BBB), since compounds showing a higher compound concentration in plasma than in the CNS implicate higher initial plasma exposures and are associated with drug-drug interactions via transporter proteins, thus limiting the use of said compounds (FDA—Clinical Drug Interaction Studies—Cytochrome P450 Enzyme- and Transporter-Mediated Drug Interactions, Guidance for industry, January 2020).

Therefore, compounds which
(i) are potent IDO1 inhibitors,
(ii) are selective over the human androgen receptor and the human Factor Xa,
(iii) have a high metabolic stability, and
(iv) have a low/no efflux,
are expected to be both efficacious in vivo and to have an acceptable safety window to be used as drugs for the treatment of diseases and conditions of CNS origin wherein IDO1 inhibition is of therapeutic benefit.

The present invention provides compounds targeting the CNS. In order to achieve substantial inhibition of the IDO1 enzyme in the CNS with a reasonable human dose (<250 mg once daily) and an acceptable safety window, the compounds of the present invention should be potent (IC50 (IDO1)<300 nM in the human whole blood assay), selective (preferably selectivity >10, more preferably selectivity >30, most preferably selectivity over the human androgen receptor and/or the human Factor Xa >30), metabolically stable (<20% QH in human hepatocytes) and have a low efflux (efflux <3) or no efflux, both in vitro and in vivo.

Surprisingly, the compounds of the present invention have been found to be potent (IC50 (IDO1)<300 nM in the human whole blood assay), selective (preferably selectivity >10, more preferably selectivity >30, most preferably selectivity over the human androgen receptor and/or the human Factor Xa >30), metabolically stable (<20% QH in human hepatocytes) and have a low efflux (efflux <3) or no efflux, both in vitro and in vivo.

Rationale for the Selection of Compounds With No or Weak P-gp Substrate Properties:

According to the free drug hypothesis, only unbound (free) drug molecules exert pharmacological effects by binding to targets. In case of drugs in therapeutic indications that require delivery to a CNS site of action, the free brain concentration is the most relevant drug concentration for in vivo CNS activity (doi: 10.1124/jpet.107.119560). Distribution of drugs to the CNS is often limited due to exclusion at the blood brain barrier (BBB). The BBB is a composed of a single layer of endothelial cells connected by tight junctions, and is characterized by low paracellular permeability, lack of fenestration and expression of multiple membrane efflux transporters, thus providing very effective protection of the CNS from circulating xenobiotics.

Therefore the desired pharmacological response of a CNS targeting drug is dependent on its passive diffusion, i.e. related to the physicochemical properties of the compound, and the relative balance between the active uptake and efflux transporters in order to overcome the neuroprotection at the BBB.

Many transporters have been identified at the BBB, of which P-gp (P-glycoprotein) is considered the most important efflux transporter due to its gatekeeper function to prevent drugs from entering the brain and its extrusion mechanism to pump out compounds that have already entered the cytoplasm of brain endothelial cells (doi: 10.1007/s11095-007-9502-2, doi: 10.1124/jpet.107.130294, /doi.org/10.1517/17460441.3.6.677).

Since P-gp plays such a critical role in limiting the uptake of drugs into the brain due to its broad substrate specificity and intrinsic transport activity, it is important to design compounds without significant P-gp efflux transport activity for CNS targets. P-gp substrate characteristics imply a reduction of its therapeutic window for CNS drug. The reduced therapeutic window results as higher free plasma concentrations are required to compensate for the efflux transport and to drive the free brain concentration to the anticipated level. However, a higher plasma concentration will increase the risk for peripheral toxicities. This supports the strategy that CNS drugs should have no substrate affinity for P-gp (doi: 10.1124/dmd.104.001230, 10.1124/jpet.107.130294).

In addition, drug-drug interactions (DDI) due to interference with BBB are likely, as observed e.g. for loperamide, a µ-opiate receptor agonist and potent P-gp substrate: Loperamide reduces gut motility by activation of peripheral µ-receptors in the intestine. Due to its high P-gp efflux, brain penetration is limited at clinical and even higher doses and its application is not associated with central opiate effects such as respiratory depression. However, co-administration of quinidine, i.e. a potent P-gp inhibitor, resulted in significant respiratory depression that does not occur after administration of loperamide alone (doi: 10.1067/mcp.2000.109156). Further examples for DDI involving P-gp at the BBB include the interaction of verapamil and cyclosporine A (doi: 10.1016/j.clpt.2005.01.022), verapamil and tariquidar (doi: 10.1038/jcbfm.2015.19), verapamil and tamoxifen (doi: 10.1124/jpet.111.180398), or etoposide and cyclosporine A (doi: 10.1002/pbc.20382), demonstrating that DDI caused by P-gp interaction at the BBB is possible in humans (doi:10.1124/dmd.112.049577).

In view of the physiological complexities of the BBB, in the in vitro preclinical screening the P-gp-transfected Madin-Darby canine kidney (MDCK) cell lines have been shown to be valuable surrogates for predicting P-gp efflux, and represent the state-of the art in vitro system (doi:

10.1016/j.ejps.2017.04.016, doi: 10.1124/dmd.116.074245). The transport characteristics of P-gp of a compound are tested in a bidirectional permeability measurement approach and are expressed by the efflux ratio. It has been demonstrated that the in vitro efflux observed in the MDCK-P-gp permeability tests correlates well with in vivo drug efflux at the BBB of rats (doi: 10.3390/pharmaceutics11110595).

Approximately 95% of CNS drugs have a P-gp efflux ratio <3 (doi: 10.1124/jpet.102.039255, 10.1080/00498250701570285), confirming that the majority of CNS drugs show no or weak P-gp mediated efflux, and that for successful CNS delivery, a compound should not be a good P-gp substrate.

Pharmaceutical Composition

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Use in Treatment/Method of Use

Human therapeutic applications of IDO1 inhibition have been summarized in reviews (doi: 10.1007/s11011-018-0290-7., doi: 10.7150/jca.31727., doi: 10.1177/1178646917691938., doi: 10.1016/j.pnpbp.2017.04.035., doi: 10.2741/4363., doi: 10.3390/molecules23010191. and doi: 10.1007/s00018-017-2504-2.).

The present invention relates to compounds which are useful in the treatment of psychiatric disorders, diseases and conditions wherein IDO1 inhibition is of therapeutic benefit, including: (1) mood disorders and mood affective disorders; (2) schizophrenia spectrum disorders; (3) neurotic, stress-related and somatoform disorders including anxiety disorders; (4) disorders of psychological development; (5) behavioral syndromes associated with physiological disturbances and physical factors; (6) substance-related and addictive disorders; (7) disease associated with symptoms of negative and positive valence, (8) neurodegenerative disorders, (9) neuro-immune disorders, (10) neurovascular disorders, (11) head trauma, (12) disorders of metabolism, (13) viral infection, (14) bacterial infection, (15) retinal diseases (16) oncology indications.

In view of their pharmacological effect, compounds of the present invention are suitable for use in the treatment of a disorder, disease or condition selected from the list consisting of (1) treatment of mood disorders and mood affective disorders including bipolar disorder I depressed, hypomanic, manic and mixed form; bipolar disorder II; depressive disorders, such as single depressive episode or recurrent major depressive disorder, minor depressive disorder, depressive disorder with postpartum onset, depressive disorders with psychotic symptoms; major depressive disorder with or without concomitant anxious distress, mixed features, melancholic features, atypical features, mood-congruent psychotic features, mood-incongruent psychotic features, and catatonia.

(2) treatment of mood disorders belonging to the schizophrenia spectrum and other psychotic disorders including schizophrenia and schizoaffective disorder with associated negative and cognitive symptoms.

(3) treatment of disorders belonging to the neurotic, stress-related and somatoform disorders including anxiety disorders, general anxiety disorder, panic disorder with or without agoraphobia, specific phobia, social phobia, chronic anxiety disorders; obsessive compulsive disorder; reaction to sever stress and adjustment disorders, such as post-traumatic stress disorder; other neurotic disorders such as depersonalisation, derealisation syndrome.

(4) treatment of disorders of psychological development including pervasive developmental disorders, including Asperger's syndrome and Rett's syndrome, autistic disorders, childhood autism and overactive disorder associated with mental retardation and stereotyped movements, specific developmental disorder of motor function, specific developmental disorders of scholastic skills, attention deficit/hyperactivity disorder.

(5) treatment of behavioral syndromes associated with physiological disturbances and physical factors including mental and behavioural disorders associated with the puerperium, including postnatal and postpartum depression; eating disorders, including anorexia nervosa and bulimia nervosa and other impulse control disorders.

(6) treatment of disorders of substance-related and addictive disorders, which are substance use disorders induced by alcohol, *cannabis*, hallucinogen, stimulant, hypnotic, tobacco.

(7) treatment of disease associated with symptoms of negative and positive valence including anhedonia, sustained threat and loss, suicidal ideation.

(8) treatment of diseases involving degeneration of neuronal and/or glial cells such as, Huntington's Disease or amyotrophic lateral sclerosis.

(9) treatment of disorders of metabolism, including obesity. This includes treatment of metabolic disorders with an ongoing chronic inflammation, and those potentially due to microbiome activity.

(10) treatment of viral infection. This includes treatment for primary purpose of normalizing T-cell function and diminishing immune tolerance, or treatment of neurological consequences of infection.

(11) treatment of bacterial infection. This includes treatment for primary purpose of normalizing T-cell function and diminishing immune tolerance, or treatment of neurological consequences of infection, or treatment of tuberculosis.

(12) treatment of retinal diseases. This includes treatment for prevention of retinal degeneration due to high IDO1 expression, as in diabetic retinopathy or geographic atrophy associated with age-related macular degeneration.

As used herein, unless otherwise noted, the terms "treating", "treatment" shall include the management and care of a human subject or human patient for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

According to another aspect, the present invention provides a compound of formula A or a pharmaceutically acceptable salt thereof for use in the treatment and/or prevention of the above mentioned conditions.

According to another aspect, the present invention provides a compound of formula A according to any one of the preceding aspects characterized in that the compound of formula is used in addition to behavioural therapy, TMS (transcranial magnetic stimulation), ECT (electroconvulsive therapy) and other therapies.

Combination Therapy

Compounds according to the present invention can be combined with other treatment options known to be used in the art in connection with a treatment of any of the indications the treatment of which is in the focus of the present invention.

According to another aspect, the present invention provides a compound of formula A according to any one of the preceding aspects characterized in that the compound of formula A is administered in addition to treatment with one or more antidepressant selected from the list consisting of duloxetine, escitalopram, bupropion, venlafaxine, desvenlafaxine, sertraline, paroxetine, fluoxetine, vortioxetine, mirtazapine, citalopram, vilazodone, trazodone, amitriptyline, clomipramine, agomelatine, levomilnacipran, lithium, doxepin, nortriptyline. The term "antidepressant" shall mean any pharmaceutical agent or drug which can be used to treat depression or diseases associated with depressive symptoms.

According to another aspect, the present invention provides a compound of formula A according to any one of the preceding aspects characterized in that the compound of formula A is administered in addition to treatment with one or more antipsychotic selected from the list consisting of aripiprazole, paliperidone palmitate, lurasidone, quetiapine, risperidone, olanzapine, paliperidone, brexpiprazole, clozapine, asenapine, chlorpromazine, haloperidol, cariprazine, ziprasidone, amisulpride, iloperidone, fluphenazine, blonanserin, aripiprazole lauroxil. The term "antipsychotic" shall mean any pharmaceutical agent or drug which can be used to treat diseases associated with psychotic or depressive symptoms.

According to another aspect, the present invention provides a compound of formula A according to any one of the preceding aspects characterized in that the compound of formula A is administered in addition to treatment with one or more psychostimulant selected from the list consisting of lisdexamphetamine, methylphenidate, amphetamine, dexamfetamine, dexmethylphenidate, armodafinil, modafinil. The term "psychostimulant" shall mean any pharmaceutical agent or drug which can be used to treat diseases like mood disorders, or impulse control disorders.

According to another aspect, the present invention provides a compound of formula A according to any one of the preceding aspects characterized in that the compound of formula A is administered in addition to treatment with nootropics selected from the list consisting of oxiracetam, piracetam, or the natural product St John's-wort.

According to another aspect, the present invention provides a compound of formula A which is administered in addition to treatment with one or more antidepressant, antipsychotic, psychostimulant, nootropics or natural product according to any one of the preceding aspects characterized in that the combination of compound of formula A and one or more antidepressant, antipsychotic, psychostimulant, nootropics or natural product is used in addition to behavioural therapy, TMS (transcranial magnetic stimulation), ECT (electroconvulsive therapy) and other therapies.

According to another aspect, the present invention provides a compound of formula A according to any one of the preceding aspects characterized in that the compound of formula A is administered in addition to treatment with any chorea suppression medication such as tetrabenazine, deutetrabenazine, and baclofen.

According to another aspect, the present invention provides a compound of formula A according to any one of the preceding aspects characterized in that the compound of formula A is administered in addition to treatment used to slow neurodegeneration such as riluzole, rasagiline and edavarone.

According to another aspect, the present invention provides a compound of formula A according to any one of the preceding aspects characterized in that the compound of formula A is administered in addition to treatment with any antiviral or antibacterial medication.

EXPERIMENTAL SECTION

Abbreviations
aq. aqueous
eq. equivalent
EtOAc ethylacetate
h hour(s)
HATU O-(7-Azabenzotriazol-1-yl)-N,N,N',N'-tetramethyluronium-hexafluorphosphate
HCl hydrochloric acid
Min minute(s)
NaOH sodium hydroxide
MeOH methanol
rt room temperature
Rt retention time
TBTU O-(Benzotriazol-1-yl)-N,N,N',N'-tetramethyluronium tetrafluoroborate
THF tetrahydrofuran
Abbreviations within spectral data
1H-NMR proton nuclear magnetic resonance
δ chemical shift
d doublet
dd doublet of doublets
DMSO-d6 hexa-deutero-dimethylsulfoxide
H proton
Hz Hertz (=1/second)
J coupling constant
m multiplet
ppm parts per million
s singlet General Analytics All reactions were carried out using commercial grade reagents and solvents. NMR spectra were recorded on a Bruker AVANCE IIIHD 400 MHz instrument using TopSpin 3.2 p16 software.

Chemical shifts are given in parts per million (ppm) downfield from internal reference trimethylsilane in δ units.

All 1H-NMR spectra were measured in DMSO-d6, unless otherwise indicated.

Selected data are reported in the following manner: chemical shift, multiplicity, coupling constants (J), integration.

Low resolution mass spectra were obtained using a liquid chromatography mass spectrometer (LCMS) that consisted of an Agilent 1100 series LC coupled to a Agilent 6130 quadrupole mass spectrometer (electrospray positive ionization).

Methods:

For solvent mixtures used for HPLC-MS methods % solvent are given as volume percent of the corresponding solvent.

HPLC-MS methods:

| Method Name: | Z011_S03 |
|---|---|
| Device description: | Agilent 1200 with DA- and MS-Detector |
| Column: | XBridge C18_3.0 × 30 mm_2.5 μm |
| Column producer: | Waters |
| Description: | |

| Gradient/ Solvent Time [min] | % Sol [Water 0.1% NH3] | % Sol [Acetonitrile] | Flow [ml/min] | Temp [° C.] | Back pressure [PSI] |
|---|---|---|---|---|---|
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Preparation of Intermediates

Intermediate 1a: 2-[(5-Bromothiophen-2-yl)formamido]-2-methylpropanoic acid

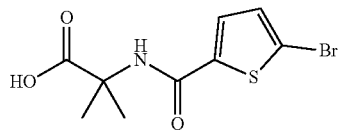

Methyl 2-[(5-bromothiophen-2-yl)formamido]-2-methylpropanoate

Under a nitrogen atmosphere at rt was added to 1.35 g (6.51 mmol) 5-bromothiophene-2-carboxylic acid in 40 mL THF 3.40 mL (19.5 mmol, 3.0 eq.) Diisopropylethylamine and 2.30 g (7.16 mmol, 1.1 eq.) TBTU. After 10 min 1.00 g (6.51 mmol, 1.0 eq.) methyl 2-aminoisobutyrate hydrochloride was added and stirring was continued at rt for 3.5 h.

The solvents were evaporated, to the residue water and EtOAc was added, the organic layer separated, washed with 5% aq. NaHCO₃-solution and twice with water and dried over Na₂SO₄. After filtration and evaporation of the solvent, the product was obtained and used for the next step without further purification.

Yield: 1.94 g (97%)
MS: 306/308 (M+H)+(Br)
1H-NMR (400 mHz): δ=1.44 (s, 6H), 7.29 (d, 1H, J=4.06 Hz), 7.70 (d, 1H, J=4.06 Hz), 8.66 (s, 1H)

2-[(5-Bromothiophen-2-yl)formamido]-2-methylpropanoic acid

To 1.80 g (5.88 mmol) Methyl 2-[(5-bromothiophen-2-yl)formamido]-2-methylpropanoate in 50 mL THF and 60 mL water was added 11.8 mL of a 1 M aq. LiOH solution. The reaction mixture was stirred overnight at rt, was concentrated to approximately 30 mL, was diluted with water and acidified with 2 M aq. HCl to pH 3-4.

The precipitate was filtered, was washed with water and dried at 50° C. to afford the desired product.

Yield: 1.61 g (94%)
MS: 292/294 (M+H)+(Br)
1H-NMR (400 mHz): δ=1.43 (s, 6H), 7.28 (d, 1H, J=3.93 Hz), 7.69 (d, 1H, J=3.93 Hz), 8.50 (s, 11H), 12.25 (s, 11H)

Intermediate 1b: 2-[(5-Chlorothiophen-2-yl)formamido]-2-methylpropanoic acid

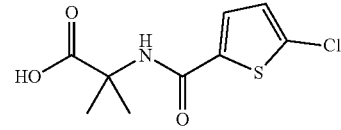

Methyl 2-[(5-chlorothiophen-2-yl)formamido]-2-methylpropanoate

To a mixture of 4.00 g (26.0 mmol) Methyl 2-aminoisobutyrate hydrochloride and 4.23 g (26.0 mmol) 5-chlorothiophene-2-carboxylic acid in 15 mL N,N-dimethylformamide was added under ice cooling 13.6 mL (78.1 mmol, 3.0 eq.) diisopropylethylamine and then in small portions 10.0 g (26.3 mmol, 1.0 eq.) HATU. The reaction mixture was stirred overnight at rt, water (100 mL) was added, the precipitate filtered, washed with water and dried in the desiccator.

Yield: 5.64 g (83%)
MS: 262/264 (M+H)+(Cl)
1H-NMR (400 mHz): δ=1.44 (s, 6H), 3.58 (s, 3H), 7.19 (d, 1H, J=4.18 Hz), 7.75 (d, 1H, J=4.06 Hz), 8.67 (s, 1H)

2-[(5-Chlorothiophen-2-yl)formamido]-2-methylpropanoic acid

To a mixture of 5.63 g (21.5 mmol) of methyl 2-[(5-chlorothiophen-2-yl)formamido]-2-methylpropanoate in 30 mL THF and 10 mL MeOH was added 6.00 mL of a 4 M aq. NaOH solution (24.0 mmol, 1.1 eq.). Stirring was continued overnight at rt. The solvents were evaporated under reduce pressure, the residue dissolved in water and acidified with 4M aq. HCl (6.0 mL). The precipitate was filtered, was washed with water, and dried in the desiccator.

Yield: 5.24 g (98%)
MS: 248/250 (M+H)+(Cl)
1H-NMR (400 mHz): δ=1.44 (s, 6H), 7.18 (d, 1H, J=4.06 Hz), 7.74 (d, 1H, J=4.18 Hz), 8.51 (s, 1H1), 12.25 (s, 11)

Exemplary Embodiments

Example 1: 2-[(5-bromothiophen-2-yl)formamido]-N-(4-chloro-3-fluorophenyl)-2-methylpropanamide

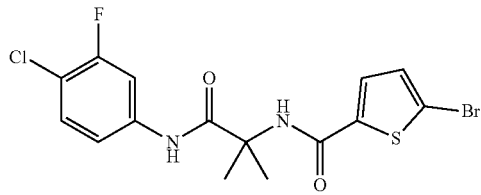 [SMILES: CC(C)(NC(=O)c1ccc(Br)s1)C(=O)Nc1ccc(Cl)c(F)c1]

At rt a mixture of 100 mg (0.34 mmol) 2-[(5-bromothiophen-2-yl)formamido]-2-methylpropanoic acid, 50 mg (0.34 mmol) 4-chloro-3-fluoroaniline and 132 μL (1.20 mmol, 3.5 eq.) 4-methylmorpholine in 3 mL THF was prepared. Then 232 μL (0.39 mmol, 1.2 eq., 50% in ethylacetate) propylphosphonic acid anhydride was added and the reaction mixture is heated overnight at 60° C. The crude reaction mixture was purified by HPLC, the product containing fractions were combined and lyophilized.

Yield: 49 mg (34%)

HPLC-MS; Method: Z011_S03; Rt [min]: 1.06

MS: 419/421/423 (M+H)+(Br/Cl)

1H-NMR (400 mHz): δ=1.50 (s, 6H), 7.31 (d, 1H, J=4.06 Hz), 7.41-7.49 (m, 2H), 7.75-7.79 (m, 2H), 8.50 (s, 1H), 9.74 (s, 1H)

Example 2: 2-[(5-bromothiophen-2-yl)formamido]-N-(4-bromophenyl)-2-methylpropanamide

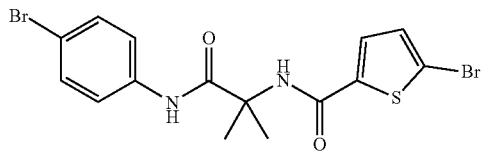 [SMILES: CC(C)(NC(=O)c1ccc(Br)s1)C(=O)Nc1ccc(Br)cc1]

At rt a mixture of 100 mg (0.34 mmol) 2-[(5-bromothiophen-2-yl)formamido]-2-methylpropanoic acid, 59 mg (0.34 mmol) 4-bromoaniline and 132 μL (1.20 mmol, 3.5 eq.) 4-methylmorpholine in 3 mL THF was prepared. Then 232 μL (0.39 mmol, 1.2 eq., 50% in ethylacetate) propylphosphonic acid anhydride was added and the reaction mixture was heated overnight at 60° C. The crude reaction mixture is purified by HPLC, the product containing fractions were combined and lyophilized.

Yield: 81 mg (53%)

HPLC-MS; Method: Z011_S03; Rt [min]: 1.05

MS: 445/447/449 (M+H)+(2 Br)

1H-NMR (400 mHz): δ=1.50 (s, 6H), 7.31 (d, 1H, J=4.06 Hz), 7.43-7.46 (m, 2H), 7.54-7.57 (m, 2H), 7.77 (d, 1H, J=4.06 Hz), 8.45 (s, 1H), 9.55 (s, 1H)

Example 3: 2-[(5-chlorothiophen-2-yl)formamido]-N-(4-chloro-3-fluorophenyl)-2-methylpropanamide

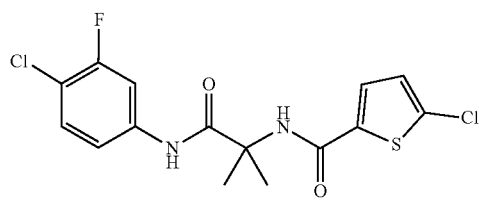 [SMILES: CC(C)(NC(=O)c1ccc(Cl)s1)C(=O)Nc1ccc(Cl)c(F)c1]

At rt a mixture of 100 mg (0.40 mmol) 2-[(5-chlorothiophen-2-yl)formamido]-2-methylpropanoic acid, 59 mg (0.40 mmol) 4-chloro-3-fluoroaniline and 155 μL (1.41 mmol, 3.5 eq.) 4-methylmorpholine in 3 mL THF was prepared. Then 274 μL (0.46 mmol, 1.2 eq., 50% in ethylacetate) propylphosphonic acid anhydride was added and the reaction mixture is heated overnight at 60° C. The crude reaction mixture was purified by HPLC, the product containing fractions were combined and lyophilized.

Yield: 62 mg (41%)

HPLC-MS; Method: Z011_S03; Rt [min]: 1.05

MS: 375/377/379 (M+H)+(2 Cl)

1H-NMR (400 mHz): δ=1.50 (s, 6H), 7.21 (d, 1H, J=4.06 Hz), 7.40-7.49 (m, 2H), 7.77 (dd, 1H, J=2.15/12.29 Hz), 7.83 (d, 1H, J=4.06 Hz), 8.51 (s, 1H), 9.74 (s, 1H)

Example 4: 2-[(5-chlorothiophen-2-yl)formamido]-N-(4-bromophenyl)-2-methylpropanamide

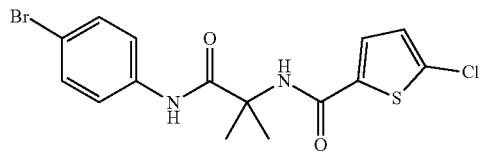 [SMILES: CC(C)(NC(=O)c1ccc(Cl)s1)C(=O)Nc1ccc(Br)cc1]

At rt a mixture of 100 mg (0.40 mmol) 2-[(5-chlorothiophen-2-yl)formamido]-2-methylpropanoic acid, 69 mg (0.40 mmol) 4-bromoaniline and 155 μL (1.41 mmol, 3.5 eq.) 4-methylmorpholine in 3 mL THF was prepared. Then 274 μL (0.46 mmol, 1.2 eq., 50% in ethylacetate) propylphosphonic acid anhydride was added and the reaction mixture is heated overnight at 60° C. The crude reaction mixture was purified by HPLC, the product containing fractions were combined and lyophilized.

Yield: 70 mg (43%)

HPLC-MS; Method: Z011_S03; Rt [min]: 1.04

MS: 401/403/405 (M+H)+(Br/Cl)

1H-NMR (400 mHz): δ=1.50 (s, 6H), 7.21 (d, 1H, J=4.06 Hz), 7.42-7.47 (m, 2H), 7.54-7.58 (m, 2H), 7.82 (d, 1H, J=4.06 Hz), 8.46 (s, 1H), 9.55 (s, 1H)

Example 5: 2-[(5-chlorothiophen-2-yl)formamido]-N-(4-chlorophenyl)-2-methylpropanamide

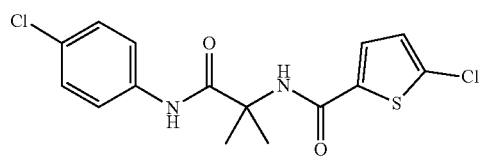 [SMILES: CC(C)(NC(=O)c1ccc(Cl)s1)C(=O)Nc1ccc(Cl)cc1]

At rt a mixture of 100 mg (0.40 mmol) 2-[(5-chlorothiophen-2-yl)formamido]-2-methylpropanoic acid, 52 mg (0.40 mmol) 4-chloroaniline and 155 μL (1.41 mmol, 3.5 eq.) 4-methylmorpholine in 3 mL THF was prepared. Then 274 μL (0.46 mmol, 1.2 eq., 50% in ethylacetate) propylphosphonic acid anhydride was added and the reaction mixture is heated overnight at 60° C. The crude reaction mixture was purified by HPLC, the product containing fractions were combined and lyophilized.

Yield: 93 mg (64%)

HPLC-MS; Method: Z011_S03; Rt [min]: 1.03

MS: 357/359/361 (M+H)+(2 Cl)

1H-NMR (400 mHz): δ=1.50 (s, 6H), 7.21 (d, 1H, J=4.06 Hz), 7.30-7.34 (m, 2H), 7.59-7.63 (m, 2H), 7.82 (d, 11H, J=4.06 Hz), 8.46 (s, 1H1), 9.55 (s, 11H1

What is claimed is:

1. A compound of formula A

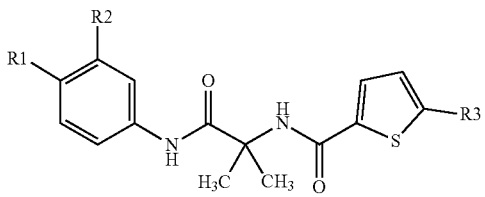

or a pharmaceutically acceptable salt thereof, wherein

R¹ represents chloro or bromo;
R² represents hydrogen or fluoro; and
R³ represents chloro or bromo.

2. The compound according to claim 1, or a pharmaceutically acceptable salt thereof, selected from the group consisting of

| Ex. | |
|---|---|
| 1 | 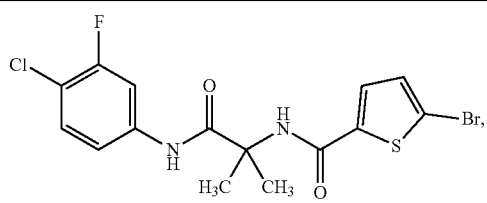 |
| 2 | 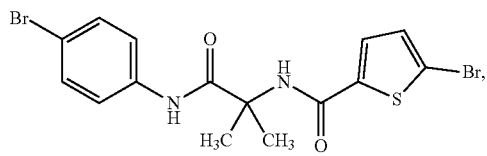 |
| 3 | 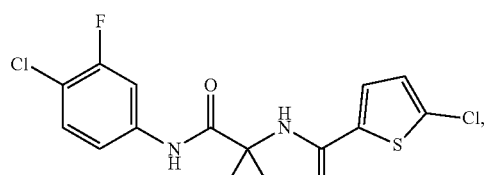 |
| 4 | 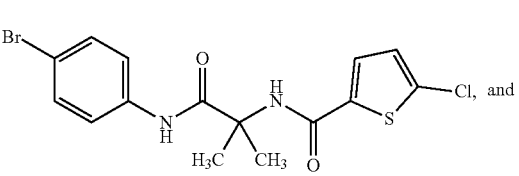 |
| 5 | 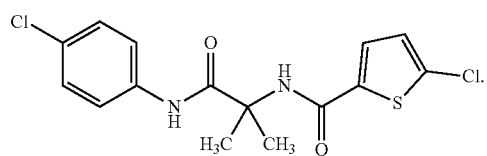 |

3. The compound according to claim 1, or a pharmaceutically acceptable salt thereof, having the structure:

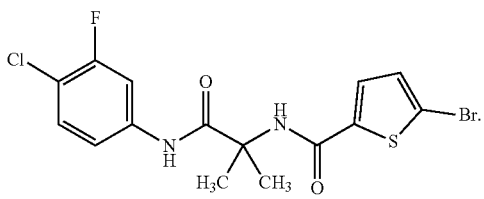 [SMILES: CC(C)(NC(=O)c1ccc(Br)s1)C(=O)Nc1ccc(Cl)c(F)c1]

4. The compound according to claim 1, or a pharmaceutically acceptable salt thereof, having the structure:

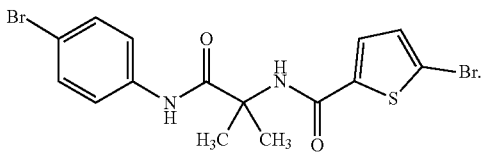 [SMILES: CC(C)(NC(=O)c1ccc(Br)s1)C(=O)Nc1ccc(Br)cc1]

5. The compound according to claim 1, or a pharmaceutically acceptable salt thereof, having the structure:

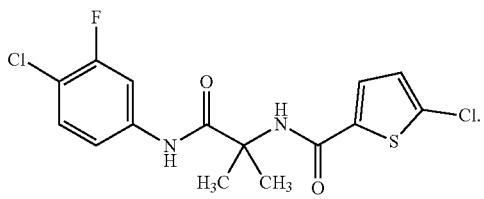

6. The compound according to claim 1, or a pharmaceutically acceptable salt thereof, having the structure:

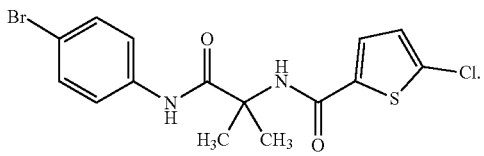 [SMILES: CC(C)(NC(=O)c1ccc(Cl)s1)C(=O)Nc1ccc(Cl)cc1]

7. The compound according to claim 1, or a pharmaceutically acceptable salt thereof, having the structure:

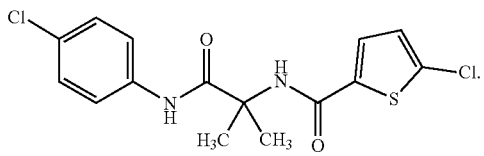

8. A pharmaceutically acceptable salt of a compound according to claim 1.

9. A method for treating a mood disorder or a mood affective disorder, comprising administering to a patient in need thereof a therapeutically effective amount of a compound according to claim 1, or a pharmaceutically acceptable salt therefore, wherein the mood disorder or mood affective disorder is selected from the group consisting of bipolar disorder I depressed, hypomanic, manic and mixed form; bipolar disorder II; depressive disorders and; major depressive disorder with or without concomitant anxious distress, mixed features, melancholic features, atypical features, mood-congruent psychotic features, mood-incongruent psychotic features, and catatonia.

10. The method according to claim 9 wherein the depressive disorder is selected from the group consisting of single depressive episode disorder, recurrent major depressive disorder, minor depressive disorder, depressive disorder with postpartum onset, and depressive disorders with psychotic symptoms.

11. The method according to claim 9, wherein the compound is administered in addition to treatment with another antidepressant drug.

12. The method according to claim 9, wherein the compound is administered in addition to behavioural therapy.

13. A pharmaceutical composition comprising the compound according to claim 1, or a pharmaceutically acceptable salt thereof, in admixture with a pharmaceutically acceptable adjuvant, diluent and/or carrier.

14. The compound according to claim 1 having the structure:

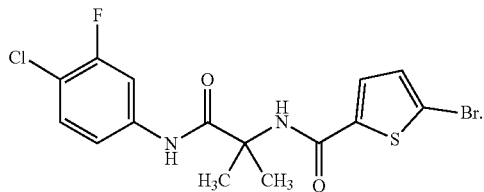

1

15. The compound according to claim 1 having the structure:

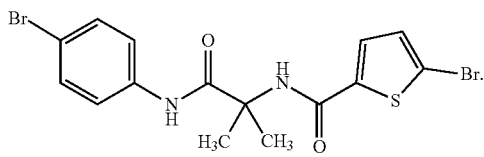

2

16. The compound according to claim 1 having the structure:

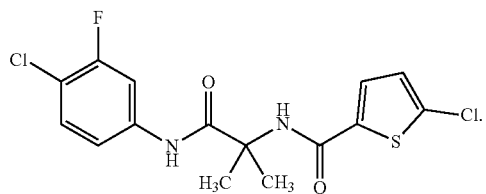

3

17. The compound according to claim 1 having the structure:

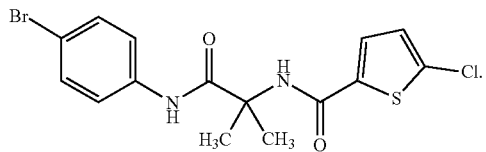

4

18. The compound according to claim 1 having the structure:

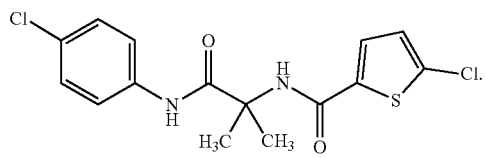

5

* * * * *